(12) United States Patent
Lomas et al.

(10) Patent No.: US 12,431,232 B2
(45) Date of Patent: Sep. 30, 2025

(54) PRESCRIPTIVE NUTRITION-BASED IV AND IM INFUSION TREATMENT FORMULA CREATION SYSTEMS AND METHODS

(71) Applicant: REVIV GLOBAL LTD, Knutsford (GB)

(72) Inventors: Sarah Lomas, Cheshire (GB); Michael Barnish, Cheshire (GB); Johnny Parvani, Phoenix, AZ (US)

(73) Assignee: REVIV GLOBAL LTD, Knutsford (GB)

( * ) Notice: Subject to any disclaimer, the term of this patent is extended or adjusted under 35 U.S.C. 154(b) by 0 days.

(21) Appl. No.: 18/391,300

(22) Filed: Dec. 20, 2023

(65) Prior Publication Data

US 2024/0120061 A1    Apr. 11, 2024

Related U.S. Application Data

(62) Division of application No. 17/880,920, filed on Aug. 4, 2022, now Pat. No. 11,894,121.

(Continued)

(51) Int. Cl.
*G16H 20/17* (2018.01)
*G16H 10/60* (2018.01)
(Continued)

(52) U.S. Cl.
CPC ............ *G16H 20/17* (2018.01); *G16H 10/60* (2018.01); *G16H 50/70* (2018.01); *G16H 70/40* (2018.01); *G16H 70/60* (2018.01)

(58) Field of Classification Search
CPC ........ G16H 20/17; G16H 10/60; G16H 50/70; G16H 70/40; G16H 70/60; G16H 10/20; G16H 10/40; G16H 40/67
(Continued)

(56) References Cited

U.S. PATENT DOCUMENTS 8,560,334 B2   10/2013  Pertti
10,929,916 B2   2/2021  Abutair
(Continued)

FOREIGN PATENT DOCUMENTS

CA    3014239    2/2020
CN    106326683   1/2017
(Continued)

OTHER PUBLICATIONS

Berthon et al., "Nutrition and Respiratory Health-Feature Review", Mar. 5, 2015, Nutrients, vol. 7, 1618-1643. (Year: 2015).
(Continued)

*Primary Examiner* — Jason B Dunham
*Assistant Examiner* — Kimberly A. Sass
(74) *Attorney, Agent, or Firm* — Kenneth C. Booth; Booth Udall, PLC

(57) ABSTRACT

A method of creating a genetically personalized intravenous or intramuscular nutrition therapy treatment formula includes developing an initial mapping of individual micronutrients to SNPs, symptoms, conditions, and therapeutic objectives based on existing individual scientific literature references that link the specific micronutrient to an SNP, a symptom, a condition, or a therapeutic objective. The method includes receiving an SNP and a symptom, a condition, or a therapeutic objective for a patient, comparing the SNP, symptom, condition, therapeutic objective combination with the initial mapping to identify matching micronutrients, creating a custom treatment formula with the identified micronutrients, and treating the patient with the formula. Feedback data about the formula's effectiveness is received and the initial mapping is updated to account for the feedback data. This process is repeated for subsequent patients positioned geographically remotely from each other (Continued)

so that future patients are treated with reference to an updated current mapping.

20 Claims, 24 Drawing Sheets

Related U.S. Application Data

(60) Provisional application No. 63/230,516, filed on Aug. 6, 2021.

(51) Int. Cl.
    *G16H 50/70*     (2018.01)
    *G16H 70/40*     (2018.01)
    *G16H 70/60*     (2018.01)

(58) Field of Classification Search
    USPC ............................................................ 705/3
    See application file for complete search history.

(56) References Cited

U.S. PATENT DOCUMENTS

| | | |
|---|---|---|
| 2002/0058712 A1 | 5/2002 | Sneed |
| 2005/0177397 A1 | 8/2005 | Kane |
| 2006/0062859 A1 | 3/2006 | Blum |
| 2006/0199155 A1 | 9/2006 | Mosher |
| 2007/0154498 A1 | 7/2007 | Bortz |
| 2008/0050740 A1 | 2/2008 | Cassidy |
| 2008/0221932 A1 | 9/2008 | Kane |
| 2009/0155381 A1 | 6/2009 | Goralczyc |
| 2009/0192365 A1 | 7/2009 | Gisel |
| 2011/0113002 A1 | 5/2011 | Kane |
| 2011/0189161 A1 | 8/2011 | Blum |
| 2012/0083669 A1 | 4/2012 | Abujbara |
| 2012/0290327 A1 | 11/2012 | Hanlon |
| 2013/0018024 A1 | 1/2013 | Bianchi |
| 2013/0216982 A1 | 8/2013 | Bennett |
| 2014/0052722 A1 | 2/2014 | Bertsimas |
| 2014/0088995 A1 | 3/2014 | Damani |
| 2015/0125462 A1 | 5/2015 | Bek |
| 2015/0269865 A1* | 9/2015 | Volach ............... G09B 19/0092 434/127 |
| 2018/0032682 A1 | 2/2018 | Donalds |
| 2018/0039759 A1 | 2/2018 | Astigarraga |
| 2018/0089385 A1 | 3/2018 | Gupta |
| 2018/0121631 A1 | 5/2018 | Mehta |
| 2018/0144820 A1 | 5/2018 | Grimmer |
| 2018/0353425 A1 | 12/2018 | Narain |
| 2018/0374567 A1 | 12/2018 | Toumazou |
| 2019/0152663 A1 | 5/2019 | Kraft |
| 2019/0221303 A1 | 7/2019 | Bennett |
| 2019/0290172 A1 | 9/2019 | Hadad |
| 2020/0135314 A1 | 4/2020 | Gostyla |
| 2021/0005304 A1* | 1/2021 | Neumann ............... G16H 50/30 |
| 2021/0005317 A1 | 1/2021 | Neumann |
| 2021/0012880 A1 | 1/2021 | Ando |
| 2021/0050086 A1* | 2/2021 | Rose ...................... G16H 20/30 |
| 2021/0134434 A1 | 5/2021 | Riley |
| 2021/0166794 A1 | 6/2021 | Nova |
| 2021/0193332 A1 | 6/2021 | Inwald |

FOREIGN PATENT DOCUMENTS

| | | |
|---|---|---|
| CN | 112069382 | 12/2020 |
| EP | 3529379 B1 | 5/2022 |
| KR | 20170054628 | 5/2017 |
| KR | 102043959 | 11/2019 |
| KR | 20190138360 | 12/2019 |
| KR | 102169661 | 10/2020 |
| KR | 20210061032 | 5/2021 |
| KR | 20210072221 | 6/2021 |
| KR | 102278646 | 7/2021 |
| WO | 2004084822 | 10/2004 |
| WO | 2012067525 | 5/2012 |
| WO | 2013086582 | 6/2013 |
| WO | WO-2013096769 A1 * | 6/2013 ......... A61B 5/14532 |
| WO | 2015004266 | 1/2015 |
| WO | WO-2015124569 A1 * | 8/2015 ............. G05B 15/02 |
| WO | 2019183404 | 9/2019 |
| WO | 2020138720 | 7/2020 |

OTHER PUBLICATIONS

Brouwer ID et al: "Reverse thinking: taking a healthy diet perspective towards food systems transformations", Food Security, Springer Netherlands, Dordrecht, vol. 13, No. 6, Oct. 16, 2021 (Oct. 16, 2021), pp. 1497-1523, XP037646513, ISSN: 1876-4517, DOI: 10.1007/SI2571-021-01204-5 [retrieved on Oct. 16, 2021].

Bujari Armir et al: "A mobile sensing and visualization platform for environmental data", Pervasive and Mobile Computing, Elsevier, NL, vol. 66, Jun. 18, 2020 (Jun. 18, 2020), XP086246547, ISSN: 1574-1192, DOI: 10.1016/J.PMCJ.2020.101204 [retrieved on Jun. 18, 2020] 11 pages.

Chen, Yu et al. Personalized Food Recommendation as Constrained Question Answering over a Large-scale Food Knowledge Graph. Rensselaer Polytechnic Institute, Troy, NY. 2021. 9 pages.

Drabsch, T. et al. A Scientific Perspective of Personalised Gene-Based Dietary Recommendations for Weight Management. Nutrients. 2019, 14 pages.

Galyean Shannon; Sawant Dhanashree; Shin Andrew C., "Personalized Nutrition for Management of Micronutrient Deficiency—Literature Review in Non-bariatric Populations and Possible Utility in Bariatric Cohort", Obesity Surgery, Rapid Communications of Oxford, Oxford,, GB, GB , (Jun. 20, 2020), vol. 30, No. 9, doi: 10.1007/s11695-020-04762-3, ISSN 0960-8923, pp. 3570-3582, XP037201002.

Ingilizian, Z. How Precision Consumption Can Improve Consumer Health and Well-Being. Forbes. Leadership Strategy. 2020, 7 pages.

Lubos, E. et al. Glutathione Peroxidase-1 in Health and Disease: From Molecular Mechanisms to Therapeutic Opportunities. Antioxid Redox Signal. 2011, 42 pages.

Maestre Mar et al: "Assessing food value chain pathways, linkages and impacts for better nutrition of vulnerable groups", Food Policy, Pergamon, Amsterdam, NL, vol. 68, Jan. 11, 2017 (Jan. 11, 2017), pp. 31-39, XP029956443, ISSN: 0306-9192, DOI: 10.1016/J.FOODPOL.2016.12.007 p. 31-p. 36; figure 1.

Matthew Metzgar et al: "The feasibility of a Paleolithic diet for low-income consumers", Nutrition Research, Elsevier, Amsterdam, NL, vol. 31, No. 6, May 14, 2011 (May 14, 2011), pp. 444-451, XP028379237, ISSN: 0271-5317, DOI: 10.1016/J.NUTRES.2011.05.008 [retrieved on May 23, 2011].

Morine Melissa J., Monteiro Jacqueline Pontes, Wise Carolyn, Teitel Candee, Pence Lisa, Williams Anna, Ning Baitang, Mccabe-Sellers Beverly, Champagne Catherine, Turner Jerome, Shelby Beatrice, Bogle Margaret, Beger Richard D., Priami Corrado, Kaput Jim, "Genetic associations with micronutrient levels identified in immune and gastrointestinal networks", Genes & Nutrition ; Studying the relationship between genetics and nutrition in the improvement of human health, Berlin ; Heidelberg : Springer, DE, DE , (Jul. 1, 2014), vol. 9, No. 4, doi: 10.1007/.

NutriGenomeDB platform, 1 page, http://www.nutrigenomedb.org/.

Poole Nigel et al: "Viewpoint: Agri-nutrition research: Revisiting the contribution of maize and wheat to human nutrition and health", Food Policy, Pergamon, Amsterdam, NL, vol. 100, Sep. 18, 2020 (Sep. 18, 2020), XP086547134, ISSN: 0306-9192, DOI: 10.1016/J.FOODPOL.2020.101976 [retrieved on Sep. 18, 2020] 13 pages.

Precision Consumer 2030 when data becomes invisible. Sparks & Honey. Culture Forecast. 2019, 125 pages.

Verkaik-Kloosterman, Janneke; Estimation of Micronutrient Intake Distributions: Development of Methods to Support Food and Nutrition Policy Making; Wageningen University and Research. ProQuest Dissertations Publishing, 2011. 28235724. (Year: 2011) 192 pages.

William A Masters et al: "The economics of malnutrition: Dietary transition and food system transformation", arxiv.org, Cornell Uni-

(56) References Cited

OTHER PUBLICATIONS versity Library, 201 OLIN Library Cornell University Ithaca, NY 14853, Feb. 5, 2022 (Feb. 5, 2022), XP091150658, abstract; table 1 p. 97.

* cited by examiner

| ICD-10 | Bloating after food | Brain Fog / Poor Concentration | Burn out/ excessive stress | Excessive Sweating | Fatigue/Low Energy | Headache | Heartburn | Hirsutism | Itching |
|---|---|---|---|---|---|---|---|---|---|
| M79.7. Fibromyalgia | | x | | | x | | | | |

| | Muscle Ache (Myalgia) | Nausea/Vomiting | Nerve Pain | Palpitations | Pins & Needles | Poor Sleep | Sunburn | Chronic Widespread Pain |
|---|---|---|---|---|---|---|---|---|
| Joint Pain | Joint Swelling | Low libido | Low mood | Mood Swings | | | | |
| x | | | | | x | x | x | | x |

Variations on components of at least one nutrient from Bag 1, 2a, and 3a — 1400

| | | | | | | | | | |
|---|---|---|---|---|---|---|---|---|---|
| Combo 1 +2a+3a.01 | NaCl 0.9% 250 ml | Alpha Lipoic Acid | B Complex | Ascorbic Acid 5g | Magnesium Sulphate 500mg | Glutathione 1.2g | NAC 500mg | Methycobalamin 1.25mg | Zinc Aspartate 5mg | Selenium 50ug |
| Combo 1 +2a+3a.03 | NaCl 0.9% 250 ml | Alpha Lipoic Acid | | Ascorbic Acid 5g | Magnesium Sulphate 500mg | Glutathione 1.2g | NAC 500mg | Methycobalamin 1.25mg | Zinc Aspartate 5mg | Selenium 50ug |
| Combo 1 +2a+3a.05 | NaCl 0.9% 250 ml | Alpha Lipoic Acid | B Complex | | Magnesium Sulphate 500mg | Glutathione 1.2g | NAC 500mg | Methycobalamin 1.25mg | Zinc Aspartate 5mg | Selenium 50ug |
| Combo 1 +2a+3a.07 | NaCl 0.9% 250 ml | Alpha Lipoic Acid | | | Magnesium Sulphate 500mg | Glutathione 1.2g | NAC 500mg | Methycobalamin 1.25mg | Zinc Aspartate 5mg | Selenium 50ug |
| Combo 1 +2a+3a.09 | NaCl 0.9% 250 ml | Alpha Lipoic Acid | B Complex | Ascorbic Acid 5g | | NAC 500mg | Glutathione 1.2g | Methycobalamin 1.25mg | Zinc Aspartate 5mg | Selenium 50ug |
| Combo 1 +2a+3a.11 | NaCl 0.9% 250 ml | Alpha Lipoic Acid | | Ascorbic Acid 5g | | NAC 500mg | Glutathione 1.2g | Methycobalamin 1.25mg | Zinc Aspartate 5mg | Selenium 50ug |
| Combo 1 +2a+3a.13 | NaCl 0.9% 250 ml | Alpha Lipoic Acid | B Complex | | | NAC 500mg | Glutathione 1.2g | Methycobalamin 1.25mg | Zinc Aspartate 5mg | Selenium 50ug |

| Variations on components of at least one nutrient from Bag 1, 2a, and 3a | | | | | | | | |
|---|---|---|---|---|---|---|---|---|
| Combo 1 +2a+3a.15 | NaCl 0.9% 250 ml | Alpha Lipoic Acid | Glutathione 1.2g | NAC 500mg | Methycobalamin 1.25mg | Zinc Aspartate 5mg | Selenium 50ug | |
| Combo 1 +2a+3a.17 | NaCl 0.9% 250 ml | Alpha Lipoic Acid | B Complex | Ascorbic Acid 5g | Magnesium Sulphate 500mg | NAC 500mg | Methycobalamin 1.25mg | Zinc Aspartate 5mg | Selenium 50ug |
| Combo 1 +2a+3a.19 | NaCl 0.9% 250 ml | Alpha Lipoic Acid | Ascorbic Acid 5g | Magnesium Sulphate 500mg | NAC 500mg | Zinc Aspartate 5mg | Selenium 50ug | |
| Combo 1 +2a+3a.21 | NaCl 0.9% 250 ml | Alpha Lipoic Acid | B Complex | Magnesium Sulphate 500mg | NAC 500mg | Methycobalamin 1.25mg | Zinc Aspartate 5mg | Selenium 50ug | |
| Combo 1 +2a+3a.23 | NaCl 0.9% 250 ml | Alpha Lipoic Acid | Magnesium Sulphate 500mg | NAC 500mg | Methycobalamin 1.25mg | Zinc Aspartate 5mg | Selenium 50ug | |
| Combo 1 +2a+3a.25 | NaCl 0.9% 250 ml | Alpha Lipoic Acid | B Complex | Ascorbic Acid 5g | Methycobalamin 1.25mg | NAC 500mg | Zinc Aspartate 5mg | Selenium 50ug | |
| Combo 1 +2a+3a.27 | NaCl 0.9% 250 ml | Alpha Lipoic Acid | Ascorbic Acid 5g | NAC 500mg | Methycobalamin 1.25mg | Zinc Aspartate 5mg | Selenium 50ug | |

FIG. 14B

| Variations on components of at least one nutrient from Bag 1, 2a, and 3a | | | | | | | |
|---|---|---|---|---|---|---|---|
| Combo 1 +2a+3a.29 | NaCl 0.9% 250 ml | Alpha Lipoic Acid | B Complex | NAC 500mg | Methycobalamin 1.25mg | Zinc Aspartate 5mg | Selenium 50ug | |
| Combo 1 +2a+3a.33 | NaCl 0.9% 250 ml | Alpha Lipoic Acid | B Complex | Ascorbic Acid 5g | Magnesium Sulphate 500mg | Glutathione 1.2g | Methycobalamin 1.25mg | Zinc Aspartate 5mg | Selenium 50ug |
| Combo 1 +2a+3a.35 | NaCl 0.9% 250 ml | Alpha Lipoic Acid | Ascorbic Acid 5g | Magnesium Sulphate 500mg | Glutathione 1.2g | Methycobalamin 1.25mg | Zinc Aspartate 5mg | Selenium 50ug |
| Combo 1 +2a+3a.37 | NaCl 0.9% 250 ml | Alpha Lipoic Acid | B Complex | Magnesium Sulphate 500mg | Glutathione 1.2g | Methycobalamin 1.25mg | Zinc Aspartate 5mg | Selenium 50ug |
| Combo 1 +2a+3a.39 | NaCl 0.9% 250 ml | Alpha Lipoic Acid | Magnesium Sulphate 500mg | Glutathione 1.2g | Methycobalamin 1.25mg | Zinc Aspartate 5mg | Selenium 50ug | |
| Combo 1 +2a+3a.41 | NaCl 0.9% 250 ml | Alpha Lipoic Acid | B Complex | Ascorbic Acid 5g | Glutathione 1.2g | Methycobalamin 1.25mg | Zinc Aspartate 5mg | Selenium 50ug |
| Combo 1 +2a+3a.43 | NaCl 0.9% 250 ml | Alpha Lipoic Acid | Ascorbic Acid 5g | Glutathione 1.2g | Methycobalamin 1.25mg | Zinc Aspartate 5mg | Selenium 50ug | |

FIG. 14C

| Variations on components of at least one nutrient from Bag 1, 2a, and 3a | | | | | | | |
|---|---|---|---|---|---|---|---|
| Combo 1 +2a+3a.45 | NaCl 0.9% 250 ml | Alpha Lipoic Acid | B Complex | Glutathione 1.2g | Methycobalamin 1.25mg | Zinc Aspartate 5mg | Selenium 50ug |
| Combo 1 +2a+3a.47 | NaCl 0.9% 250 ml | Alpha Lipoic Acid | Glutathione 1.2g | Methycobalamin 1.25mg | Zinc Aspartate 5mg | Selenium 50ug | |
| Combo 1 +2a+3a.49 | NaCl 0.9% 250 ml | Alpha Lipoic Acid | B Complex | Ascorbic Acid 5g | Magnesium Sulphate 500mg | Methycobalamin 1.25mg | Zinc Aspartate 5mg |
| Combo 1 +2a+3a.51 | NaCl 0.9% 250 ml | Alpha Lipoic Acid | Ascorbic Acid 5g | Magnesium Sulphate 500mg | Methycobalamin 1.25mg | Zinc Aspartate 5mg | Selenium 50ug |
| Combo 1 +2a+3a.53 | NaCl 0.9% 250 ml | Alpha Lipoic Acid | B Complex | Magnesium Sulphate 500mg | Methycobalamin 1.25mg | Zinc Aspartate 5mg | Selenium 50ug |
| Combo 1 +2a+3a.55 | NaCl 0.9% 250 ml | Alpha Lipoic Acid | Magnesium Sulphate 500mg | Methycobalamin 1.25mg | Zinc Aspartate 5mg | Selenium 50ug | |
| Combo 1 +2a+3a.57 | NaCl 0.9% 250 ml | Alpha Lipoic Acid | B Complex | Ascorbic Acid 5g | Methycobalamin 1.25mg | Zinc Aspartate 5mg | Selenium 50ug |

| Variations on components of at least one nutrient from Bag 1, 2a, and 3a | | | | | | | |
|---|---|---|---|---|---|---|---|
| Combo 1 +2a+3a.59 | NaCl 0.9% 250 ml | Alpha Lipoic Acid | Ascorbic Acid 5g | Methycobalamin 1.25mg | Zinc Aspartate 5mg | Selenium 50ug | | |
| Combo 1 +2a+3a.61 | NaCl 0.9% 250 ml | Alpha Lipoic Acid | B Complex | Methycobalamin 1.25mg | Zinc Aspartate 5mg | Selenium 50ug | | |
| Combo 1 +2a+3a.65 | NaCl 0.9% 250 ml | Alpha Lipoic Acid | B Complex | Ascorbic Acid 5g | Magnesium Sulphate 500mg | Glutathione 1.2g | | |
| Combo 1 +2a+3a.67 | NaCl 0.9% 250 ml | Alpha Lipoic Acid | Ascorbic Acid 5g | Magnesium Sulphate 500mg | Glutathione 1.2g | NAC 500mg | Zinc Aspartate 5mg | Selenium 50ug |
| Combo 1 +2a+3a.69 | NaCl 0.9% 250 ml | Alpha Lipoic Acid | B Complex | Magnesium Sulphate 500mg | Glutathione 1.2g | NAC 500mg | Zinc Aspartate 5mg | Selenium 50ug |
| Combo 1 +2a+3a.71 | NaCl 0.9% 250 ml | Alpha Lipoic Acid | Magnesium Sulphate 500mg | Glutathione 1.2g | NAC 500mg | Zinc Aspartate 5mg | Selenium 50ug | |
| Combo 1 +2a+3a.73 | NaCl 0.9% 250 ml | Alpha Lipoic Acid | B Complex | Ascorbic Acid 5g | Glutathione 1.2g | NAC 500mg | Zinc Aspartate 5mg | Selenium 50ug |

FIG. 14E

| Variations on components of at least one nutrient from Bag 1, 2a, and 3a | | | | | | | | |
|---|---|---|---|---|---|---|---|---|
| Combo 1 +2a+3a.75 | NaCl 0.9% 250 ml | Alpha Lipoic Acid | Ascorbic Acid 5g | Glutathione 1.2g | NAC 500mg | Zinc Aspartate 5mg | Selenium 50ug | |
| Combo 1 +2a+3a.77 | NaCl 0.9% 250 ml | Alpha Lipoic Acid | B Complex | Glutathione 1.2g | NAC 500mg | Zinc Aspartate 5mg | Selenium 50ug | |
| Combo 1 +2a+3a.79 | NaCl 0.9% 250 ml | Alpha Lipoic Acid | Glutathione 1.2g | NAC 500mg | Zinc Aspartate 5mg | Selenium 50ug | | |
| Combo 1 +2a+3a.81 | NaCl 0.9% 250 ml | Alpha Lipoic Acid | B Complex | Ascorbic Acid 5g | Magnesium Sulphate 500mg | NAC 500mg | Zinc Aspartate 5mg | Selenium 50ug |
| Combo 1 +2a+3a.83 | NaCl 0.9% 250 ml | Alpha Lipoic Acid | Ascorbic Acid 5g | Magnesium Sulphate 500mg | NAC 500mg | Zinc Aspartate 5mg | Selenium 50ug | |
| Combo 1 +2a+3a.85 | NaCl 0.9% 250 ml | Alpha Lipoic Acid | B Complex | Magnesium Sulphate 500mg | NAC 500mg | Zinc Aspartate 5mg | Selenium 50ug | |

FIG. 14F

Oral/IM:

1. H. Badsha, M. Daher, and K. Ooi Kong, 'Myalgias or non-specific muscle pain in Arab or Indo-Pakistani patients may indicate vitamin D deficiency', Clin. Rheumatol., vol. 28, no. 8, pp. 971–973, Aug. 2009, doi: 10.1007/s10067-009-1146-7.

Patients who were diagnosed with fibromyalgia and/or non-specific musculoskeletal pain were screened for vitamin D deficiency. Those with severe vitamin D deficiency (<15 ng/dl) were treated with either high-dose vitamin D3 injections (600,000 IU i.m. single dose) or oral vitamin D3 tablets 50,000 IU weekly for 8 weeks. Alpha calcidol 1 mg daily with follow-up in 1 month was used for the treatment of patients with levels between 16 and 20 ng/dl. 90% of patients reported clinical improvement. However, serum 25(OH)D after supplementation was not reported in this study.

2. N. T. Abokrysha, 'Vitamin D Deficiency in Women with Fibromyalgia in Saudi Arabia', Pain Med., vol. 13, no. 3, pp. 452–458, Mar. 2012, doi: 10.1111/j.1526-4637.2011.01304.x.

Female patients with fibromyalgia and a mean vitamin D level of 4.76 ± 1.46 ng/mL were treated with either high-dose vitamin D3 injections (600,000 IU intramuscular [im] single dose) or oral vitamin D3 tablets 50,000 IU weekly for 8 weeks. Patients demonstrated significant clinical improvement (ACR criteria). It should be noted that, no controls were included in this study and the concentrations of 25(OH)D were not available after supplementation.

PRESCRIPTIVE NUTRITION-BASED IV AND IM INFUSION TREATMENT FORMULA CREATION SYSTEMS AND METHODS

RELATED APPLICATIONS

This application is a divisional of U.S. Utility application Ser. No. 17/880,920, filed Aug. 4, 2022, which application claims the benefit of U.S. Provisional Application No. 63/230,516, filed Aug. 6, 2021, the disclosures of which are hereby incorporated by reference in its entirety.

TECHNICAL FIELD

This disclosure relates generally to intravenous ("IV") and intramuscular ("IM") nutrition therapy, and more specifically to a process for creating formulas for use in IV and IM nutrition therapy that target specific diseases, symptoms, medical conditions, and/or therapeutic objectives. The formulas may be custom formulas that are personalized to the recipient based on genetic data. The IV and IM nutrition therapy formulas may also or alternatively be customized/personalized based on other medical data.

BACKGROUND

Achieving and maintaining optimal health and proper function of the human body requires proper nutrition and hydration, including a correct balance of nutrients such as macronutrients (e.g., proteins, carbs, fats) and micronutrients (e.g., vitamins, minerals, antioxidants). An increasingly popular method of achieving this balance is through IV and IM delivery of the nutrients. IV and IM delivery are generally more efficient than oral intake of the same nutrients, leading to a more effective treatment. Currently, IV and IM nutrition therapies use generic formulations, with the same formulation used for each individual, regardless of the individual's specific needs. Because each individual is unique and has different requirements for nutrients and because each disease treatment is unique and has different requirements for nutrients, what is beneficial to one person with one particular disease may be less useful, or even detrimental, to another with a different genetic make-up and disease. Thus, current IV and IM nutrition therapies may provide excess unnecessary nutrients or omit vital ingredients, resulting in suboptimal supplementations and less effective therapy.

SUMMARY

Aspects of this disclosure relate to a method of creating a genetically personalized intravenous or intramuscular nutrition therapy treatment formula, the method comprising developing an initial mapping of each of a plurality of individual micronutrients to a single nucleotide polymorphism (SNP) and to at least one of a symptom, a condition, and a therapeutic objective, the developing the initial mapping comprising, for each specific micronutrient of the plurality of individual micronutrients: creating an individual score for each of a plurality of existing individual scientific literature references that links the specific micronutrient to an SNP, a symptom, a condition, or a therapeutic objective; adding the individual scores for each of the plurality of existing individual scientific literature references for the specific micronutrient with respect to each combination of an SNP and at least one of a symptom, a condition, and a therapeutic objective; and determining that the specific micronutrient matches the SNP and the at least one of a symptom, a condition, and a therapeutic objective when the individual scores for the specific micronutrient with respect to the SNP and the at least one of a symptom, a condition, and a therapeutic objective add up to more than a predetermined threshold; storing the initial mapping, the individual scores, and the added scores in a database; receiving an SNP for a first patient and at least one of a symptom, a condition, and a therapeutic objective for the first patient; comparing the SNP for the first patient and the at least one of a symptom, a condition, and a therapeutic objective for the first patient with the initial mapping stored in the database to identify one or more micronutrients that have been matched to the SNP for the first patient and the at least one of a symptom, a condition, and a therapeutic objective for the first patient; creating a custom intravenous or intramuscular nutrition therapy treatment formula for the first patient, wherein the identified one or more micronutrients are ingredients of the custom intravenous or intramuscular nutrition therapy treatment formula, and wherein a dosage of each of the identified one or more micronutrients is selected based on the SNP of the first patient and the at least one of a symptom, a condition, and a therapeutic objective for the first patient; treating the first patient with the custom intravenous or intramuscular nutrition therapy treatment formula; receiving feedback data about an effectiveness of the custom intravenous or intramuscular nutrition therapy treatment formula in addressing the at least one of a symptom, a condition and a therapeutic objective for the first patient; creating an individual treatment score for the identified one or more micronutrients in the custom intravenous or intramuscular nutrition therapy treatment formula with respect to the SNP for the first patient and the at least one of a symptom, a condition, and a therapeutic objective for the first patient based on the feedback data; updating the initial mapping by: adding the individual treatment score for the identified one or more micronutrients in the custom intravenous or intramuscular nutrition therapy treatment formula to the added scores stored in the database that are associated with the identified one or more micronutrients, the SNP for the first patient, and the at least one of a symptom, a condition, and a therapeutic objective for the first patient; comparing the updated added scores with the predetermined threshold to reevaluate whether there are matches for the identified one or more micronutrients in the custom intravenous or intramuscular nutrition therapy treatment formula; and storing the updated initial mapping, the individual treatment score, and the updated added scores in the database; and for each of a plurality of subsequent patients positioned geographically remotely from each other: receiving an SNP of the subsequent patient and at least one of a symptom, a condition, and a therapeutic objective of the subsequent patient; comparing the SNP for the subsequent patient and the at least one of a symptom, a condition, and a therapeutic objective for the subsequent patient with a current mapping stored in the database to identify one or more micronutrients that have been matched to the SNP for the subsequent patient and the at least one of a symptom, a condition, and a therapeutic objective for the subsequent patient, wherein the current mapping has been updated with the individual treatment score of the first patient and individual treatment scores of any other previously treated patient; creating a custom intravenous or intramuscular nutrition therapy treatment formula for the subsequent patient, wherein the identified one or more micronutrients are ingredients of the custom intravenous or intramuscular nutrition therapy treatment formula, and wherein a dosage of each of the identified one or more micronutrients is selected based on the SNP of the subsequent patient and the at least one of a symptom, a condition, and a therapeutic objective for the subsequent patient; treating the subsequent patient with the custom intravenous or intramuscular nutrition therapy treatment formula; receiving feedback data about an effectiveness of the custom intravenous or intramuscular nutrition therapy treatment formula in addressing the at least one of a symptom, a condition and a therapeutic objective for the subsequent patient; creating an individual treatment score for the identified one or more micronutrients in the custom intravenous or intramuscular nutrition therapy treatment formula with respect to the SNP for the subsequent patient and the at least one of a symptom, a condition, and a therapeutic objective for the subsequent patient based on the feedback data; updating the current mapping by: adding the individual treatment score for the identified one or more micronutrients in the custom intravenous or intramuscular nutrition therapy treatment formula for the subsequent patient to current added scores stored in the database that are associated with the identified one or more micronutrients, the SNP for the subsequent patient, and the at least one of a symptom, a condition, and a therapeutic objective for the subsequent patient; comparing the updated current added scores with the predetermined threshold to reevaluate whether there are matches for the identified one or more micronutrients in the custom intravenous or intramuscular nutrition therapy treatment formula for the subsequent patient; and storing the updated current mapping, the individual treatment score of the subsequent patient, and the updated current scores in the database; and treating future patients with reference to the updated current mapping.

Particular implementations may comprise one or more of the following features. Updating the current mapping based on individual scores for each of a plurality of new individual scientific literature references. A reference of the plurality of existing individual scientific literature references that is statistically significant and positively links a micronutrient to an SNP, a symptom, a condition, or a therapeutic objective has an individual score greater than zero. A reference of the plurality of existing individual scientific literature references that is statistically significant and negatively links a micronutrient to an SNP, a symptom, a condition, or a therapeutic objective has an individual score less than zero. A reference of the plurality of existing individual scientific literature references that relates to an injectable outcome has an individual score that has more weight than an individual score of a reference of the plurality of existing individual scientific literature references that relates to an oral outcome. A reference of the plurality of existing individual scientific literature references that is not statistically significant has an individual score less than zero.

Aspects of this disclosure relate to a method of creating a genetically personalized intravenous or intramuscular nutrition therapy treatment formula, the method comprising: (a) creating a personalized nutrition therapy formula creation algorithm and storing the personalized nutrition therapy formula creation algorithm in a database; (b) receiving medical information, genetic information, and therapeutic objectives of a patient as inputs for the personalized nutrition therapy formula creation algorithm, wherein the genetic information comprises genetic test results and the medical information comprises blood test results, vital signs, medical histories, medical diagnoses, current symptoms, diseases of which the patient is at heightened risk, or family history; (c) creating a custom intravenous or intramuscular nutrition therapy treatment formula from the personalized nutrition therapy formula creation algorithm based on the medical information, genetic information, and therapeutic objectives, wherein ingredients of the custom intravenous or intramuscular nutrition therapy treatment formula comprise one or more micronutrients identified by the personalized nutrition therapy formula creation algorithm as a match for the medical information, genetic information, and therapeutic objectives based on individual scores stored in the database of a plurality of existing individual scientific literature references relating to the one or more micronutrients and individual treatment scores stored in the database of previous intravenous or intramuscular nutrition therapy treatments comprising the one or more micronutrients; (d) treating the patient with the custom intravenous or intramuscular nutrition therapy treatment formula; (e) receiving feedback data about results of the custom intravenous or intramuscular nutrition therapy treatment formula on the patient, wherein the feedback data comprises feedback about measured bloodwork, epigenetic changes, improvements or declines in symptoms, progress towards reaching therapeutic objectives, vital signs, overall health and fitness, or physical or mental energy; (f) creating an individual treatment score for the custom intravenous or intramuscular nutrition therapy treatment formula on the patient based on the feedback data and entering the individual treatment score electronically into a computer system associated with the database so that the individual treatment score is stored in the database; (g) updating the personalized nutrition therapy formula creation algorithm to incorporate the individual treatment score for the custom intravenous or intramuscular nutrition therapy treatment formula on the patient for subsequent patients; (h) creating future custom intravenous or intramuscular nutrition therapy treatment formulas based on the updated personalized nutrition therapy formula creation algorithm, wherein the updated personalized nutrition therapy formula creation algorithm is configured to create custom intravenous or intramuscular nutrition therapy treatment formulas comprising micronutrients that most closely match patient needs based on all available patient medical information, genetic information, and therapeutic objectives, and most current aggregated feedback based on real patients with similar genes and symptoms; and (i) repeating steps (b)-(h) for subsequent patients to create a feedback loop of automatically applying patient therapy feedback data to the personalized nutrition therapy formula creation algorithm so that all new custom intravenous or intramuscular nutrition therapy treatment formulas are created based on the feedback data received from all previous patients who received custom intravenous or intramuscular nutrition therapy treatment formulas through the personalized nutrition therapy formula creation algorithm, wherein at least some of the patient and the subsequent patients are positioned geographically remotely from each other.

Particular implementations may comprise one or more of the following features. The therapeutic objectives of the patient may comprise at least one of health goals, aesthetic goals, fitness goals, weight loss, increased energy, healthier skin, healthier hair, and improved mental acuity. The personalized nutrition therapy formula creation algorithm may be configured to map the medical information and the genetic information to a code. The code may comprise a selection from the International Classification of Diseases. The personalized nutrition therapy formula creation algorithm comprises multiple algorithms in sequence. The medical information comprises at least one current symptom and at least one condition. The medical information of the patient comprises a first symptom and the genetic information of the patient comprises a first gene, wherein medical information of at least one of the subsequent patients comprises the first symptom and genetic information of the at least one of the subsequent patients comprises a second gene different than the first gene, and wherein the one or more micronutrients of the custom intravenous or intramuscular nutrition therapy treatment formula for the patient comprises a first micronutrient and a custom intravenous or intramuscular nutrition therapy treatment formula for the at least one of the subsequent patients comprises a second micronutrient different than the first micronutrient.

Aspects of this disclosure relate to a system for creating a genetically personalized intravenous or intramuscular nutrition therapy treatment formula, the system comprising: a plurality of genetic testing kits, each testing kit configured to determine genetic information of one of a plurality of patients, the plurality of patients positioned geographically remotely from each other; a plurality of electronic devices, each electronic device configured to receive the genetic information of one of the plurality of patients, medical information of the one of the plurality of patients, and therapeutic objectives of the one of the plurality of patients; and a server comprising a database storing a personalized nutrition therapy formula creation algorithm, wherein the server is configured to wirelessly receive the genetic information, the medical information, and the therapeutic objectives of each of the plurality of patients, wherein the server is configured to, for each of the plurality of patients: output to the electronic device a custom intravenous or intramuscular nutrition therapy treatment formula for the patient from the personalized nutrition therapy formula creation algorithm based on the medical information, genetic information, and therapeutic objectives of the patient, wherein the ingredients of the custom intravenous or intramuscular nutrition therapy formula comprise one or more micronutrients identified by the personalized nutrition therapy formula creation algorithm as a match for the medical information, genetic information, and therapeutic objectives of the patient based on individual scores stored in the database of a plurality of existing individual scientific literature references relating to the one or more micronutrients and individual treatment scores stored in the database of previous intravenous or intramuscular nutrition therapy treatments comprising the one or more micronutrients; receive feedback data about results of the custom intravenous or intramuscular nutrition therapy treatment formula after the patient has been treated based on the custom intravenous or intramuscular nutrition therapy treatment formula, wherein the feedback data comprises feedback about measured bloodwork, epigenetic changes, improvements or declines in symptoms, progress towards reaching therapeutic objectives, vital signs, overall health and fitness, or physical or mental energy; create an individual treatment score based on the feedback data and store the individual treatment score in the database; update the personalized nutrition therapy formula creation algorithm to incorporate the individual treatment score for subsequent patients; and create future custom intravenous or intramuscular nutrition therapy treatment formulas based on the updated personalized nutrition therapy formula creation algorithm, wherein the updated personalized nutrition therapy formula creation algorithm is configured to create custom intravenous or intramuscular nutrition therapy treatment formulas comprising micronutrients that most closely match patient needs based on all available patient medical information, genetic information, and therapeutic objectives, and most current aggregated feedback based on real patients with similar genes and symptoms.

Particular implementations may comprise one or more of the following features. The therapeutic objectives comprise health goals, aesthetic goals, fitness goals, weight loss, increased energy, healthier skin, healthier hair, or improved mental acuity. The personalized nutrition therapy formula creation algorithm is configured to map the medical information and the genetic information to a code. The code comprises a selection from the International Classification of Diseases. The personalized nutrition therapy formula creation algorithm comprises multiple algorithms in sequence. The medical information comprises at least one current symptom and at least one condition. The medical information of a first patient of the plurality of patients comprises a first symptom and the genetic information of the first patient comprises a first gene, wherein the medical information of a second patient of the plurality of patients comprises the first symptom and the genetic information of the second patient comprises a second gene different than the first gene, and wherein the one or more micronutrients of the custom intravenous or intramuscular nutrition therapy treatment formula for the first patient comprises a first micronutrient and the one or more micronutrients of the custom intravenous or intramuscular nutrition therapy treatment formula for the second patient comprises a second micronutrient different than the first micronutrient.

The foregoing and other aspects, features, applications, and advantages will be apparent to those of ordinary skill in the art from the specification, drawings, and the claims. Unless specifically noted, it is intended that the words and phrases in the specification and the claims be given their plain, ordinary, and accustomed meaning to those of ordinary skill in the applicable arts. The inventors are fully aware that he can be his own lexicographer if desired. The inventors expressly elect, as their own lexicographers, to use only the plain and ordinary meaning of terms in the specification and claims unless they clearly state otherwise and then further, expressly set forth the "special" definition of that term and explain how it differs from the plain and ordinary meaning. Absent such clear statements of intent to apply a "special" definition, it is the inventors' intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112(f). Thus, the use of the words "function," "means" or "step" in the Detailed Description or Description of the Drawings or claims is not intended to somehow indicate a desire to invoke the special provisions of 35 U.S.C. § 112(f), to define the invention. To the contrary, if the provisions of 35 U.S.C. § 112(f) are sought to be invoked to define the inventions, the claims will specifically and expressly state the exact phrases "means for" or "step for", and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventors not to invoke the provisions of 35 U.S.C. § 112(f). Moreover, even if the provisions of 35 U.S.C. § 112(f) are invoked to define the claimed aspects, it is intended that these aspects not be limited only to the specific structure, material or acts that are described in the preferred embodiments, but in addition, include any and all structures, materials or acts that perform the claimed function as described in alternative embodiments or forms of the disclosure, or that are well known present or later-developed, equivalent structures, material or acts for performing the claimed function.

The foregoing and other aspects, features, and advantages will be apparent to those of ordinary skill in the art from the specification, drawings, and the claims.

BRIEF DESCRIPTION OF THE DRAWINGS

The disclosure will hereinafter be described in conjunction with the appended drawings.

FIG. 13 shows a chart linking a diagnostic code to symptoms and conditions according to some embodiments.

FIGS. 14A-14F show a chart of formulas created through the processes disclosed herein according to some embodiments.

FIG. 17A shows a listing of scientific literature according to some embodiments.

DETAILED DESCRIPTION

Figure 1:
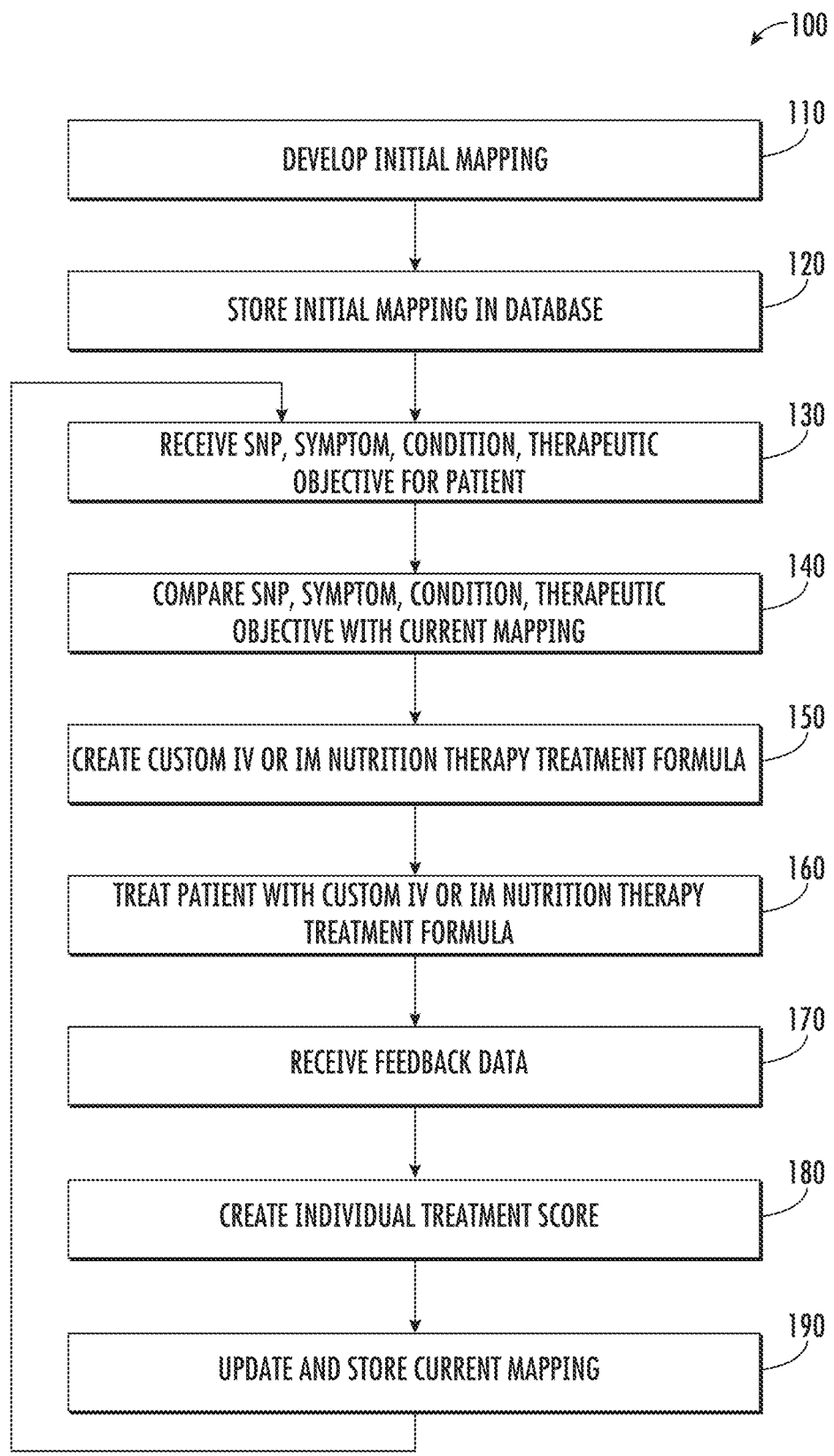
FIG. 1 shows a process flow for creating custom IV or IM nutrition therapy treatment formulas according to some embodiments.

This disclosure, its aspects and implementations, are not limited to the specific components, methods, or other examples disclosed herein. Many additional components, methods, and procedures known in the art are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The word "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented but have been omitted for purposes of brevity.

While this disclosure includes a number of implementations in many different forms, the drawings show particular implementations that will be described in detail with the understanding that the present disclosure is to be considered as an exemplification of the principles of the disclosed methods and systems and is not intended to limit the broad aspect of the disclosed concepts to the implementations illustrated.

Achieving and maintaining optimal health and proper function of the human body requires proper nutrition and hydration, including a correct balance of nutrients such as macronutrients (e.g., proteins, carbs, fats) and micronutrients (e.g., vitamins, minerals, antioxidants). An increasingly popular method of achieving this balance is through IV and IM delivery of the nutrients. IV and IM delivery are generally more efficient than oral intake of the same nutrients, leading to a more effective treatment. Currently, IV and IM nutrition therapies use generic formulations, with the same formulation used for each individual, regardless of the individual's specific needs. Because each individual is unique and has different requirements for nutrients and because each disease treatment is unique and has different requirements for nutrients, what is beneficial to one person with one particular disease may be less useful, or even detrimental, to another with a different genetic make-up and disease. Thus, current IV and IM nutrition therapies may provide excess unnecessary nutrients or omit vital ingredients, resulting in suboptimal supplementations and less effective therapy.

The present disclosure describes systems and methods that provide prescriptive nutritional therapy formulation methods and systems based on nutritional life science research. The resulting custom nutrition therapy treatment formulations may provide genetically personalized IV and IM nutrition therapies. In some embodiments, the nutrition therapies are also or alternatively personalized based on other medical data. Because the therapy disclosed herein is appropriate for each individual recipient based on their genetic code, diagnosed disease, symptomology, and therapeutic outcomes, it may be uniquely designed to meet each individual's nutritional needs. As will be described in more detail below, these individual needs may be determined based on genetic data and test results, medical history, and/or medical data and test results, among other things. Thus, each recipient of the prescriptive nutritional therapy can receive the correct balance and amount of nutrients, including macronutrients (e.g., proteins, carbs, fats) and micronutrients (e.g., vitamins, minerals, electrolytes, antioxidants) that will best help address symptoms, target therapeutic outcomes, and any disease or condition with which they have been diagnosed. Some implementations may focus on only some of these nutrients and may include nutrients not listed as well.

In some embodiments, the systems and methods disclosed herein facilitate determining which nutrients are needed for certain combinations of genetic information and medical information. For example, micronutrients may be matched to certain genetic information (e.g., a gene, a single nucleotide polymorphism ("SNP"), a genotype, etc.), symptoms, conditions, therapeutic objectives, and/or combinations of these attributes based on existing scientific literature. The matching of micronutrients to genetic information, symptoms, conditions, and/or therapeutic objectives may be repeatedly updated based on outcomes of the nutrition therapies, which may facilitate nutrition therapies to become more and more personalized to a patient's specific situation.

Updating micronutrient matches is not limited to a single patient's past nutrition therapy, nor is it limited to patients of a single medical professional or healthcare provider. Rather, the methods and systems allow for updating micronutrient matches for any patients that will receive nutrition therapy in the future as soon as an outcome of a nutrition therapy is received by the system, even if these patients are positioned geographically remotely from each other (i.e., they are treated in different parts of the world (e.g., different neighborhood, city, county, state, country, etc.) or by different healthcare providers). Thus, the systems and methods may create custom IV or IM nutrition therapy treatment formulas with micronutrients that most closely match patient needs based on all available patient medical information, genetic information, and therapeutic objectives, and most current aggregated feedback based on real patients with similar genes and symptoms. In some embodiments, the methods and systems create a feedback loop of automatically applying patient therapy feedback data so that all new custom IV or IM nutrition therapy treatment formulas include the feedback data received from all previous IV or IM nutrition therapy patients who received custom IV or IM nutrition therapy treatment formulas through the system.

The present disclosure thus also relates to improvements to the formulas used in nutritional therapy to create and apply each formula more accurately. Recipients of the nutritional therapies disclosed herein may experience improved disease prevention and treatment, slowing and/or prevention of aging, maintenance of metabolic function, achievement of weight, fitness and cosmetic goals, and improved growth and development as a result of the nutritional therapy. Each of the components discussed herein may be implemented alone, or in conjunction with each of the other described components.

In some embodiments, custom IV and IM therapy formulas may be created by collecting medical and genetic data regarding the recipient, analyzing the medical and genetic data to determine the nutritional needs of the recipient (e.g., based on a nutritional formulary mapping nutrients to various medical and genetic data), creating a custom formula based on the nutritional needs of the recipient, administering the custom formula to the recipient through IV or IM treatment, collecting feedback from the recipient regarding the effect of the IV or IM treatment, and adjusting the nutritional formulary to incorporate the feedback provided.

Any medical and genetic data can be relevant. Therefore, to provide the nutritional therapies disclosed herein, the data collected may include, but is not limited to, blood test results, genetic test results, vital signs (e.g., blood pressure, heart rate, heart rhythm, etc.), biometric data, data received from wearable devices, lifestyle data (such as travel and recent infections or vaccinations), medical histories, medical diagnoses, diseases of which the recipient is at heightened risk, and current symptom descriptions. In addition, the data may include specific therapeutic objectives of the recipient, such as health goals, aesthetic goals, fitness goals, weight loss, increased energy, healthier skin or hair, or improved mental acuity (or others discussed below). As more data is included, the nutritional therapies can be adapted to be more comprehensive and accurate in providing the nutritional needs for the specific recipient, and for refining the processes for creating nutritional therapy formulations for other recipients with similar genetic make-ups, conditions or diseases, and desired therapeutic outcomes.

The medical and genetic data may be provided directly by the recipient or may be determined using medical and lab procedures. In some embodiments, some of the medical and genetic data is provided directly by the recipient and some of the medical and genetic data is determined using medical and lab procedures. For example, the recipient may provide a family medical history and a description of current symptoms, such as fatigue or headaches, while medical tests and procedures may be used to perform blood tests and genetic tests, as well as provide a medical diagnosis.

In some embodiments, the collected data may be mapped into a code to facilitate the interpretation of the data and enable its use in algorithms and automated systems. For example, an international classification system may be used, such as the International Statistical Classification of Diseases and Related Health Problems (ICD) implemented by the World Health Organization (WHO). The most current ICD code is the ICD-11. Any system of classification of diseases, symptoms, and genes may be implemented.

The collected data may be analyzed to determine the nutritional needs of the recipient. In some implementations of the nutritional therapies disclosed herein, the collected data is analyzed by a life science professional who is familiar with the genes, diseases, and symptoms communicated by the data and understands what nutritional needs this data expresses. For example, experts in fields such as nutraceuticals, pharmacokinetics, pharmaceuticals, nutrition, nutritional science, nutrigenomics, biomedical sciences, food data sciences, and statistics may work together to review the collected data and determine which nutrients can help improve the health of the recipient.

In other implementations, this analysis may be automated. For example, a nutritional formulary or a mapping may be created which links each gene, disease, symptom, and therapeutic objective with different nutritional needs (e.g., micronutrients). Additionally, the nutritional formulary may indicate nutritional needs for specific combinations of symptoms, diseases, genes, and therapeutic objectives. For example, a first recipient may have a first symptom and a first gene. The nutritional formulary may suggest a first micronutrient to provide what the first recipient needs. A second recipient may have the same first symptom, but a second gene. In some cases, the nutritional formulary may suggest the same first micronutrient in the same amount. However, in other cases, the specific combination of the first symptom with the second gene may necessitate suggesting a second micronutrient or a different amount of the first micronutrient. Thus, the nutritional formulary is configured to take into account all of the collected data in determining the nutritional needs of the recipient to identify a therapy formulation best suited for the recipient based on current research results discovered through feedback from others receiving similar therapies. The nutritional formulary may be stored in a nutritional database. All references herein to a nutritional formulary may be considered a reference to a nutritional database. Likewise, all references to a nutritional database may be considered a reference to a nutritional formulary. The nutritional formulary or nutritional database may also be referred to as a mapping (i.e., mapping micronutrients to genetic information, symptoms, conditions, therapeutic objectives, and combinations of these attributes). The nutritional formulary may be used by an automated process or may be used by the experts discussed above.

Once the nutritional needs of the recipient have been determined, a custom formula may be created for administration to the recipient. As mentioned above, ingredients of the custom formula (and their amounts) may be selected based on the nutritional needs of the recipient. For example, specific amounts and combinations of different nutrients may be included in the formula to target the specific needs and goals of the recipient. In some embodiments, the custom formula comprises modifying a preexisting formula by adding an ingredient (e.g., a micronutrient) or by modifying an amount of one or more ingredients. The formula (whether custom or preexisting) may also be modified to meet the nutritional needs of the recipient so that the overall process of creating treatment formulas improves over time. The formula may be administered to the recipient through an IV treatment or an IM treatment. Alternatively, the nutritional therapy may also be administered orally or topically. It will be understood that any IV treatment referenced herein may also be implemented as an IM treatment, an oral treatment, or a topical treatment. Additionally, the nutritional therapy may be administered through a combination of different treatments. For example, the recipient may receive therapy through an IV treatment and an IM treatment, or any other combination. The recipient may travel to a clinic or other setting to receive the treatment.

Feedback may be collected from the recipient regarding the recipient's experience after receiving the treatment. For example, the recipient may provide feedback about any change (improvements or declines) in symptoms, vital signs, overall health and fitness, or physical or mental energy. The recipient may also provide feedback about progress towards reaching therapeutic objectives. Other types of feedback may also be received. For example, feedback may originate from measured bloodwork, epigenetic changes, or other sources. This feedback can then be used as a helpful datapoint in determining the effectiveness of the treatment and whether each of the ingredients used in the custom formula had the desired effect. In some embodiments, with multiple datapoints collected from various recipients, the nutritional database can be updated and improved.

In some embodiments, the formulas (whether custom or preexisting) may be modified based on the feedback. For example, a first recipient with a particular diagnosis may find success in achieving optimum health through receiving treatments with a first micronutrient, while a second recipient with the same diagnosis may not be successful on the first micronutrient. Over time, with enough datapoints from recipients with the same diagnosis, it may be discovered that a particular gene interferes with the effectiveness of the first micronutrient, but that a second micronutrient can have the same effect. Once the nutritional database is updated to reflect this finding, the nutritional therapy becomes more effective. For this reason, the feedback loop provides an important benefit.

In a particular implementation, the recipient's genetic micronutrient requirement profile may be generated to illustrate the specific nutrients needed. This micronutrient requirement profile may be generated based on the collected data. Based on the recipient's micronutrient requirement profile, the IV or IM therapy can be personalized to provide the recipient with vital ingredients in the amounts necessary. Moving forward, the personalized formula can be sequentially refined based on the recipient's goals combined with diagnostics to reach the desired outcomes of proper nutrition and optimal health.

As mentioned above, in particular embodiments, instead of simply updating the standard formulas or creating a new formula that is then available to multiple recipients, the nutritional database may be used to create completely custom formulas from existing components, uniquely designed for a specific recipient. In such an embodiment, the feedback collected from the recipient may be used to refine the nutritional database to aid in creating more accurate custom formulas for others as well, or in refining the established therapy formulas and components. By combining the knowledge gathered through research regarding the effect of nutritional ingredients with the diagnostics collected from recipients, the algorithm embodied in the nutritional database can be refined, helping to create more effective custom formulas (which may lead to improved standard formulas and help develop improved new formulas).

Thus, one implementation of creating an IV therapy treatment comprises collecting medical and genetic data regarding the recipient, analyzing the medical and genetic data to determine the nutritional needs of the recipient, creating a custom formula based on the nutritional needs of the recipient, administering the formula to the recipient through IV or IM treatment, collecting feedback from the recipient regarding the effect of the IV or IM treatment, adjusting the nutritional database to incorporate the feedback provided, and creating an updated formula based on the nutritional needs of the recipient and the feedback provided by the recipient.

Another implementation of prescribing an IV treatment may comprise identifying nutrient ingredients that can be administered intravenously, developing a library of scientific evidence or a nutritional database linking each nutrient ingredient to a code of a classification system corresponding to specific symptoms, genes, diseases, and/or therapeutic objectives, receiving data regarding a specific recipient's symptoms, genes, diseases, and/or therapeutic objectives, assigning codes from the classification system to the recipient based on the data received, and identifying appropriate nutrient ingredients for the recipient based on the assigned codes. The appropriate nutrient ingredients may then be used to either create a new custom formula to be administered to the recipient, or to match the recipient with a standard formula that most closely matches the nutritional needs of the recipient.

An example method 100 of providing genetically personalized IV or IM nutrition therapy with custom IV or IM nutrition therapy treatment formulas is shown, for example, in FIG. 1. Although method 100 as shown in FIG. 1 includes a number of operations in a particular order, method 100 may include more or fewer operations and the operations may be completed in different orders. In addition or alternatively, in some embodiments, variations of the operations shown in FIG. 1 may be used as part of method 100.

In some embodiments, method 100 includes developing an initial mapping of genetic and/or medical data to micronutrients based on existing scientific literature at operation 110, storing the initial mapping in a database at operation 120, receiving genetic data (e.g., a single nucleotide polymorphism (SNP), a genome, gene, multiple SNPs, etc.) and/or medical data (e.g., symptoms, conditions, therapeutic objectives, vital signs, etc.) of a patient at operation 130, comparing the genetic and medical data with the current mapping (e.g., the initial mapping or an updated mapping based on feedback from previous treatments and/or new scientific literature) at operation 140, creating a custom IV or IM nutrition therapy treatment formula based on the comparison at operation 150, treating the patient with the custom IV or IM nutrition therapy treatment formula at operation 160, receiving feedback data based on the treatment at operation 170, creating an individual treatment score for that treatment based on the feedback at operation 180, and updating and storing the current mapping based on the individual treatment score at operation 190. The method 100 may include repeating operations 130, 140, 150, 160, 170, 180, and 190 for multiple patients that are geographically remote from each other.

Thus, in some embodiments, because feedback from patient treatments is constantly being used to update the mapping, the mapping will be more up to date than existing published science alone. In some embodiments, new scientific literature may be inputted to update the mapping, in addition to the feedback from patient treatments. Inputting both scientific literature and feedback from patient treatments helps keep the mapping as up to date as possible and contributes to greater accuracy and more personalization in the mapping.

In some embodiments, at operation 110, the initial mapping of genetic and/or medical data to micronutrients is developed. The mapping identifies the micronutrients that are suitable for patients having particular genetics, particular symptoms, particular conditions, or particular therapeutic objectives based on the existing scientific literature. As discussed further below, the micronutrients may be mapped to various combinations of genetics, symptoms, conditions, and therapeutic objectives. For example, the micronutrients may be mapped to particular genetics, a particular symptom, a particular condition, and a particular therapeutic objective. The genetic data may be an SNP, a genome, a gene, multiple SNPs, or some other genetic data. The discussion below primarily refers to an SNP, but the same principles apply to using other types of genetic data and the disclosure includes other types of genetic data.

Figure 2:
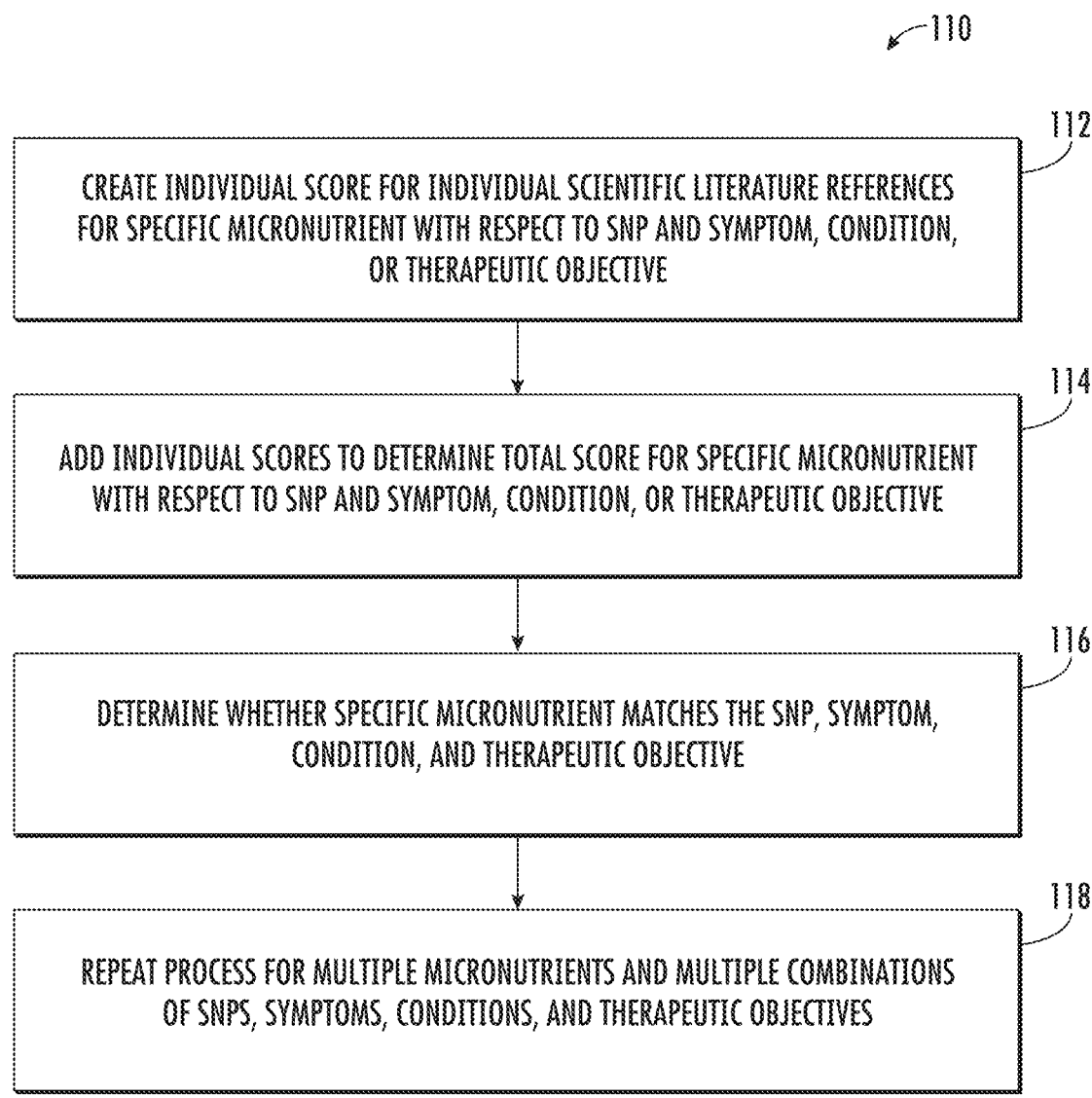
FIG. 2 shows a process flow for developing an initial mapping of micronutrients to genetic information, symptoms, conditions, and therapeutic objectives according to some embodiments.

An example process for operation 110 of developing an initial mapping is shown in FIG. 2. In some embodiments, at operation 112, an individual score is created for individual scientific literature references for a specific micronutrient with respect to an SNP (or some other type of genetic data) and a symptom, condition, or therapeutic objective (or a combination of a symptom, condition, and/or therapeutic objective). An individual score may be created for every available scientific literature reference. A reference may have multiple individual scores if the reference discusses multiple micronutrients, multiple SNPs, multiple symptoms, multiple conditions, or multiple therapeutic objectives. For example, the reference may receive an individual score for each unique combination of micronutrient, SNP, symptom, condition, and/or therapeutic objective discussed in the reference.

An individual score may be positive or negative. A positive score is created when the individual scientific literature reference provides evidence of a positive connection between a micronutrient and an SNP, symptom, condition, therapeutic objective, or a combination of two or more of these characteristics. A negative score is created when the individual scientific literature reference provides evidence of a negative connection between a micronutrient and an SNP, symptom, condition, therapeutic objective, or a combination of two or more of these characteristics. In some embodiments, a scientific literature reference that provides a non-statistically significant outcome may also receive a negative score.

In some embodiments, the individual score may be zero. For example, in some embodiments, a score of zero may be created for references that provide a non-statistically significant outcome. In some embodiments, only studies that have a statistical significance assessment are scored. For example, case series and reports may be logged but do not affect the scoring, due to a low level of scientific evidence. On the other hand, randomized controlled trials, meta-analyses, and observational studies may be scored.

In some embodiments, the individual score may be weighted based on various factors. For example, the individual score may be weighted based on the strength of the findings in the reference, the number of categories (e.g., SNP, symptom, condition, therapeutic objective) analyzed in the reference, or the category that had a connection (e.g., a connection for an SNP may be weighted higher than a connection for a therapeutic objective, etc.). Other factors may also be used. As one example, in some embodiments, a reference that relates to an injectable outcome may be given an individual score that has more weight than an individual score of a reference that relates to an oral outcome.

In some embodiments, at operation 114, individual scores relating to a specific micronutrient may be added together to determine a total score for the specific micronutrient with respect to an SNP (or some other type of genetic data) and a symptom, condition, or therapeutic objective (or a combination of a symptom, condition, and/or therapeutic objective). In some embodiments, at operation 116, it is determined whether the specific micronutrient matches the SNP, symptom, condition, and therapeutic objective. For example, if the total score for the micronutrient with respect to the SNP, symptom, condition, and therapeutic objective exceeds a predetermined threshold, then the micronutrient is determined to match the SNP, symptom, condition, and therapeutic objective. This may be repeated for each combination of SNP, symptom, condition, and therapeutic objective so that the method identifies all the scenarios for which the specific micronutrient is a good match.

Figure 3:
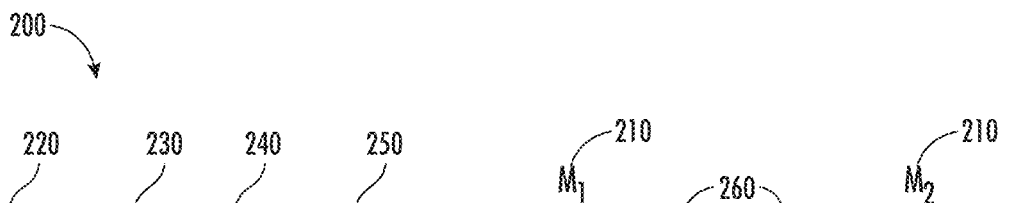
FIG. 3 shows a representative initial mapping of micronutrients to genetic information, symptoms, conditions, and therapeutic objectives according to some embodiments.

In some embodiments, at operation 118, this scoring process (i.e., operations 112, 114, and 116) is repeated for multiple micro-nutrients and multiple combinations of SNPs, symptoms, conditions, and therapeutic objectives to develop the initial mapping. A schematic representing an example initial mapping 200 is shown in FIG. 3. For simplicity, FIG. 3 only shows two micronutrients ($M_1$ and $M_2$), two SNPs ($SNP_1$ and $SNP_2$), two symptoms ($S_1$ and $S_2$), two conditions ($C_1$ and $C_2$), and two therapeutic objectives ($TO_1$ and $TO_2$). However, initial mapping 200 may include many more micronutrients, SNPs, symptoms, conditions, and/or therapeutic objectives.

The schematic of initial mapping 200 includes mapping columns 210 that include series of cells 260 that indicate whether the micronutrient matches the combination of SNP, symptom, condition, and therapeutic objective in that particular row. A checkmark indicates a match. To the left of mapping columns 210 are an SNP column 220, a symptom column 230, a condition column 240, and a therapeutic objective column 250. In some embodiments, changing the SNP, symptom, condition, or therapeutic objective (and keeping the other factors the same) may result in a different recommended micronutrient. In some embodiments, multiple micronutrients may be matched with the same combination of SNP, symptom, condition, and therapeutic objective.

In some embodiments, the initial mapping 200 provides a specific dosage of a micronutrient for a specific combination of SNP, symptom, condition, and therapeutic objective, in addition to identifying which micronutrient is a match. In particular, when scientific literature provides evidence of the right amount of a micronutrient to use for a particular SNP, symptom, condition, and/or therapeutic objective, this detail may be included in the mapping. In some embodiments, scientific literature providing evidence of a dosage may be scored to determine the recommended dosage. In some embodiments, the dosage evidence is not scored, but is simply used as a guideline (until further information becomes available through patient treatments and feedback about the results).

In some embodiments, there may be holes in the initial mapping 200. For example, there may not be sufficient scientific literature for a certain micronutrient, SNP, symptom, condition, or therapeutic objective to determine whether there is a good match. In some embodiments, the method may include making a best guess based on similar or related micronutrients, SNPs, symptoms, conditions, or therapeutic objectives. As discussed below, method 100 refines the results continuously over time. In some embodiments, the initial mapping may begin less specific (e.g., the recommended micronutrient is the same for a given symptom, condition, and therapeutic objective regardless of genetic information) with the mapping becoming more specific as process 100 is used (e.g., the recommended micronutrient for a given symptom, condition, and therapeutic objective differs depending on genetic information). The increased specificity is not limited to genetic information, but may also be based on symptoms, conditions, and/or therapeutic objectives. For example, the initial mapping may map a micronutrient to a given SNP, symptom, and condition, regardless of the therapeutic objective, while the mapping may be updated through process 100 so that the recommended micronutrient for the given SNP, symptom, and condition differs depending on the therapeutic objective.

In some embodiments, the mapping relates solely to genetic information (e.g., SNPs) and suitable IV or IM micronutrients (potentially including dosage and frequency). Feedback through patient treatments may likewise focus solely on genetic information rather than considering medical information in addition to genetic information. In some embodiments, the mapping relates solely to clinical presentations (e.g., symptoms or conditions) and suitable IV or IM micronutrients (potentially including dosage and frequency). In some embodiments, any combination of genetic information, medical information, symptoms, conditions, and therapeutic objectives (including each one individually) may be mapped to suitable IV or IM micronutrients (potentially including dosage and frequency). This same principle applies to other implementations disclosed herein. Specifically, the methods and systems disclosed herein may focus only on SNPs in identifying suitable micronutrients, only on clinical presentations, only on symptoms, only on conditions, only on therapeutic objectives, or any combination of these factors.

In addition, while the method of FIG. 1 focuses on custom treatment formulas for IV or IM nutrition therapy, in some embodiments, the mapping may be to oral supplement nutrients, and in particular to oral supplement micronutrients. This same principle applies to other implementations disclosed herein. Specifically, the methods and systems disclosed herein may relate to oral supplement treatments instead of IV or IM nutrition therapy. In the context of oral supplements treatments, again, the mapping may be of clinical presentations to oral supplement micronutrients, SNPs to oral supplement micronutrients, or a combination of clinical presentation and SNPs to oral supplement micronutrients.

Returning to FIG. 1, in some embodiments, at operation 120, the initial mapping 200 is stored in a database. In some embodiments, the individual scores of the scientific literature references for each micronutrient, SNP, symptom, condition, and therapeutic objective combination are also stored in the database. The added scores (or the total scores) for each micronutrient, SNP, symptom, condition, and therapeutic objective combination may also be stored in the database. The database may be part of a server and made available over a network to electronic devices, as discussed in more detail below with respect to FIGS. 10 and 11. The electronic devices accessing the database over the network may be patient electronic devices, healthcare provider electronic devices, or both (see FIG. 11). Because the initial mapping 200 is stored in a database available over a network, the mapping can be updated in real time by patient treatments that occur in different geographic locations and by different healthcare providers through the remaining operations of method 100. Although the remaining operations of method 100 are described for a single patient, these operations may be repeated many times for multiple patients to update the mapping and improve the accuracy of the mapping.

In some embodiments, at operation 130, an SNP, symptom, condition, or therapeutic objective are received for a patient. In some embodiments, all four of an SNP, symptom, condition, and therapeutic objective are received. In some embodiments, only a subset of an SNP, symptom, condition, and therapeutic objective are received. For example, an SNP for a patient and at least one of a symptom, a condition, and a therapeutic objective of a patient may be received (e.g., SNP and symptom; SNP and condition; SNP and therapeutic objective; SNP, symptom, and condition; etc.). Multiple SNPs, symptoms, conditions, and therapeutic objectives may be received for the patient. For example, if the patient has multiple symptoms, each symptom may be included. This information may be entered into fields on an electronic device by the patient or by the healthcare provider. In some embodiments, a patient may have a profile that stores information from previous treatments. When a patient comes in for another treatment, the system may automatically retrieve the stored information (e.g., regarding SNPs, symptoms, conditions, therapeutic objectives). Because symptoms, conditions, and therapeutic objectives may change over time, the patient may either confirm or edit this information.

In some embodiments, the SNP, symptom, condition, or therapeutic objective may be determined by a test kit or monitoring equipment. For example, a genetic testing kit may be used to determine the patient's genetic information, including an SNP. Additional examples of monitoring equipment that may determine symptoms or conditions (or contribute to determining a therapeutic objective) include thermometers, scales, blood pressure monitors, blood glucose monitors, heart rate monitors, pulse oximeters, electrocardiographs, etc.

After receiving the patient's SNP, symptom, condition, and therapeutic objective (or a subset, such as an SNP and at least one of a symptom, condition, and therapeutic objective), this information may be compared with the current mapping stored in the database at operation 140. For the first patient, the current mapping may be the initial mapping 200. Once feedback from patient treatments has been received, the current mapping may be an updated mapping based on that feedback. Comparing the patient's information with the current mapping identifies one or more micronutrients that have been matched to the SNP, symptom, condition, and therapeutic objective (or a subset, such as an SNP and at least one of a symptom, condition, and therapeutic objective).

In some embodiments, at operation 150, a custom IV or IM nutrition therapy treatment formula may be created for the patient based on the one or more micronutrients identified from the current mapping (e.g., initial mapping 200 or an updated mapping). Creating a formula may comprise determining the ingredients (and the amounts) for a formula. In some embodiments, creating the formula also comprises actually making a batch of the custom formula. For example, the identified one or more micronutrients may be the ingredients of the custom treatment formula. In some embodiments, the identified one or more micronutrients are the only ingredients of the custom treatment formula. In some embodiments, the identified one or more micronutrients may be ingredients that are added to an existing formula. In some embodiments, the identified one or more micronutrients are the primary active ingredients and are combined with a normal saline solution. In some embodiments, the mapping may also determine the dosage of the identified one or more micronutrients for the custom formula. For example, a dosage of each of the identified one or more micronutrients may be selected based on the SNP of the first patient and the at least one of a symptom, a condition, and a therapeutic objective for the first patient. Additional examples of creating custom formulas are discussed below.

In some embodiments, the mapping may suggest that an existing formula is what a patient needs. Thus, in some embodiments, an IV or IM nutrition therapy is determined by selecting an existing IV or IM nutrition therapy formula that includes a specific dosage of at least one of the identified micronutrients. For example, there may be a plurality of IV or IM nutrition therapy formulas to choose from, and the formula that provides the identified micronutrients may be selected. In some embodiments, the formula that not only provides the identified micronutrients, but also provides the right amount of the identified micronutrients is selected.

In some embodiments, creating a custom treatment formula comprises selecting an existing IV or IM nutrition therapy formula that most closely provides the identified micronutrients and modifying the formula to better provide the identified micronutrients. In some embodiments, creating a custom formula comprises specifically creating an IV or IM nutrition therapy formula (e.g., from scratch) that includes the identified micronutrients. Creating an IV or IM nutrition therapy treatment formula may include determining an IV or IM nutrition therapy formula to administer (using one of the approaches discussed above), determining a dosage or amount of the formula to administer, determining a frequency of administering the formula, and/or determining a number of times to administer the formula.

At operation 160, the patient is treated with the custom IV or IM nutrition therapy treatment formula created at operation 150. In some embodiments, at operation 170, feedback data relating to the custom IV or IM nutrition therapy treatment formula is received. The feedback data may be about an effectiveness of the custom IV or IM nutrition therapy treatment formula in addressing the symptom, the condition, or the therapeutic objective of the patient (or a subset of the symptom, condition, and therapeutic objective).

In some embodiments, the feedback data may include objective feedback (e.g., test results) and/or subjective feedback (e.g., survey responses). For example, the feedback data may include feedback about measured bloodwork (e.g., comparing bloodwork from before and after the IV or IM nutrition therapy), epigenetic changes, improvements or declines in symptoms, progress towards reaching therapeutic objectives, vital signs, overall health and fitness, or physical or mental energy. Other types of feedback may also be used.

In some embodiments, at operation 180, an individual treatment score is created based on the feedback data. The individual treatment score may be for the identified one or more micronutrients in the IV or IM nutrition therapy with respect to the patient's SNP and symptom, condition, and therapeutic objective (or a subset). Similar to the scores for scientific literature, individual treatment scores may be positive or negative. For example, when the custom IV or IM nutrition therapy treatment formula results in improvement in the symptom, a positive individual treatment score may be created. On the other hand, if the symptom worsens, a negative score may be created. The individual treatment score may be based on a single factor (e.g., whether the symptom improved or declined), or the score may be based on multiple factors (e.g. change in symptom(s), progress for reaching therapeutic objective, vital signs, energy levels, etc.).

In addition, individual treatment scores may be weighted depending on the feedback data. For example, the individual treatment score may be commensurate with how much a symptom improves or declines and/or how much progress is made (or lost) towards reaching a therapeutic objective. Thus, the more the symptom improves, the higher the individual treatment score will be. As another example, the more progress is made towards the therapeutic objective, the higher the individual treatment score will be.

In some embodiments, multiple individual treatment scores may be created for a single treatment. For example, if a symptom declines but progress is made toward a therapeutic objective, a negative score may be made for the combination of the SNP, symptom, and therapeutic objective while a positive score may be made for the combination of the SNP and therapeutic objective without that symptom.

In some embodiments, individual treatment scores may be weighted based on multiple factors. Certain factors may have greater weight than others. For example, whether the symptom improves may have greater weight than measured bloodwork or vice versa.

Figure 4:
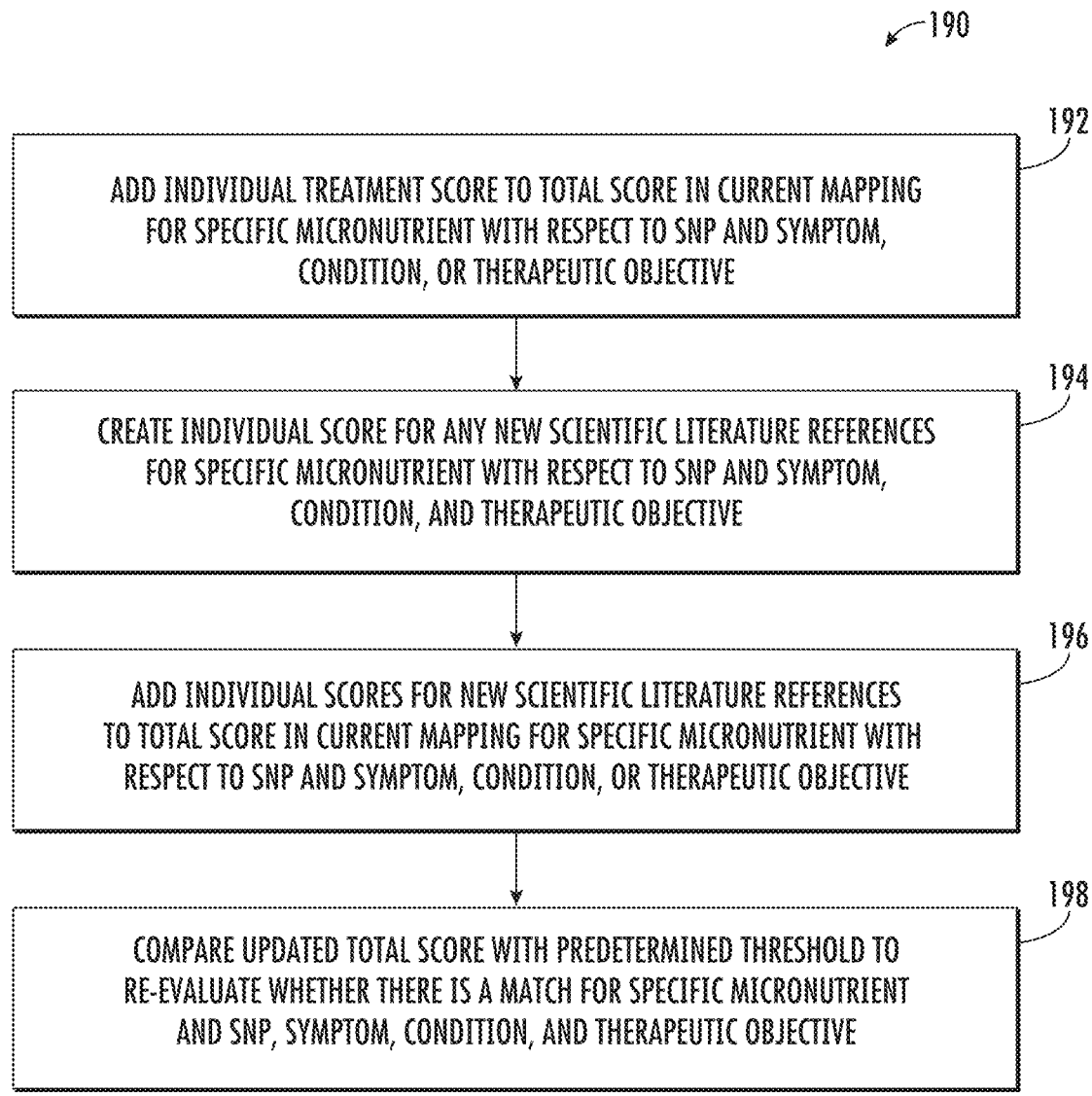
FIG. 4 shows a process flow for updating a mapping of micronutrients to genetic information, symptoms, conditions, and therapeutic objectives according to some embodiments.

In some embodiments, at operation 190, the current mapping is updated and then stored in the database. As noted above, for the first patient, the current mapping may be the initial mapping 200. Once feedback from patient treatments has been received, the current mapping may be an updated mapping based on that feedback. An example process for operation 190 of updating a current mapping is shown in FIG. 4.

In some embodiments, at operation 192, an individual treatment score (e.g., from treatment of a first patient) is added to a total score in the current mapping (e.g., initial mapping 200) for the specific micronutrient(s) used in the treatment with respect to the SNP and symptom, condition, and therapeutic objective (or a subset) of the patient being treated. To illustrate this principle, if a patient is treated having a GPx1 gene SNP, a headache as a symptom, fibromyalgia as a condition, and weight loss as a therapeutic objective, the individual treatment score may be tied to this combination of SNP, symptom, condition, and therapeutic objective. Thus, this individual treatment score would be added to the total score from the current mapping of the GPx1 gene SNP, headache symptom, fibromyalgia condition, and weight loss therapeutic objective.

In some embodiments, at operation 194, an individual score is created for any new scientific literature references that have not previously been taken into account (to the extent there are any). Thus, if a new study has linked a specific micronutrient to an SNP, symptom, condition, or therapeutic objective (or a combination of some or all of these), an individual score is created for each relevant combination of micronutrient, SNP, symptom, condition, and therapeutic objective. The principles discussed above for creating individual scores for scientific literature references equally apply to any new references.

In some embodiments, at operation 196, the individual scores for any new scientific literature references are added to the total score in the current mapping (in addition to the added individual treatment scores added in operation 192). The updated total score (based on the addition in operation 192 and/or operation 196) may be stored in the database.

In some embodiments, at operation 198, the updated total score is compared with a predetermined threshold (e.g., the same predetermined threshold used when evaluating the total score to develop the initial mapping 200). This comparison allows for reevaluating whether there is a match between a specific micronutrient and an SNP, symptom, condition, and therapeutic objective combination. This process of updating the current mapping ensures that the mapping is based on the latest scientific literature and real time results of actual treatment. Similar comparisons may be made to determine appropriate dosage, frequency, etc. of the nutrition therapy (e.g., of a specific micronutrient or of a custom treatment formula).

In some embodiments, fewer or more operations than are shown in FIG. 4 may be used to update a current mapping. For example, the mapping may be updated based only on patient treatments, only on new scientific literature references, or a combination of patient treatments and scientific literature references. The order of the operations may differ from what is shown in FIG. 4.

Figure 5:
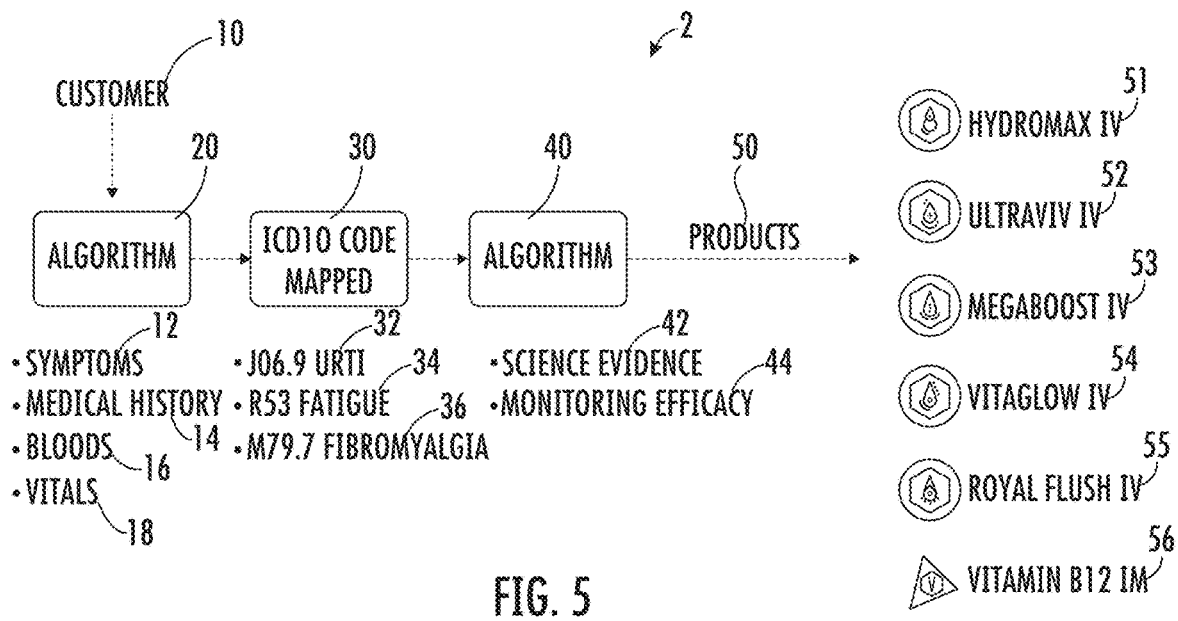
FIG. 5 shows a schematic of providing genetically personalized IV or IM nutrition therapy according to some embodiments.
Figure 6:
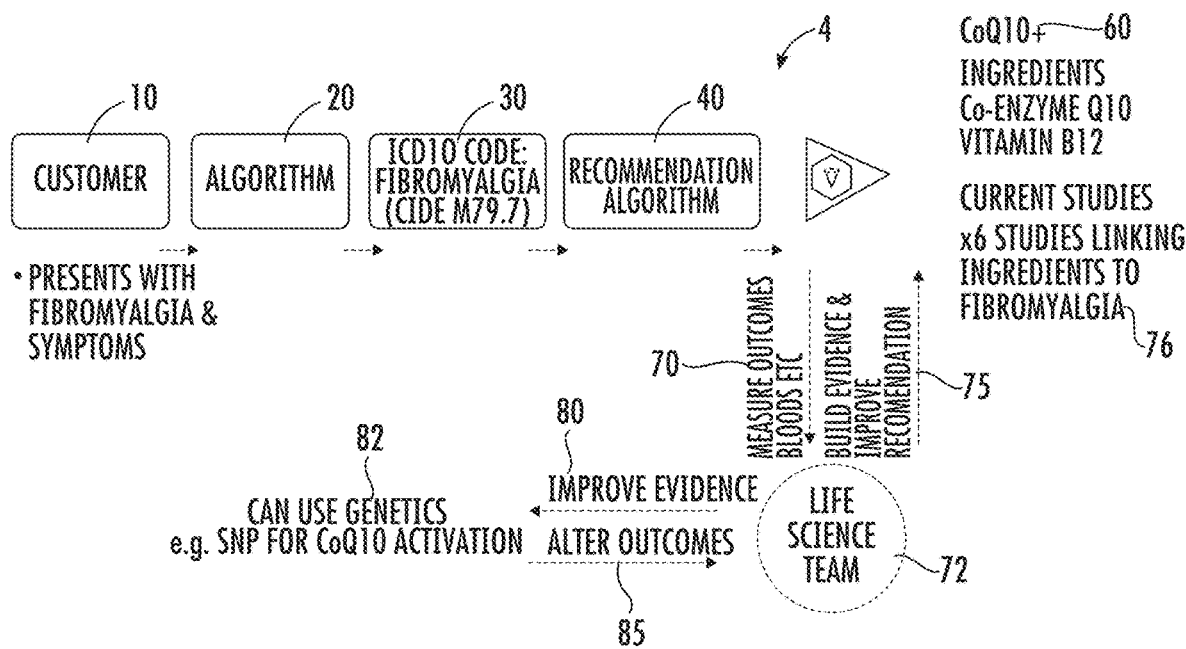
FIG. 6 shows a schematic of providing genetically personalized IV or IM nutrition therapy to target a specific disease according to some embodiments.
Figure 7:
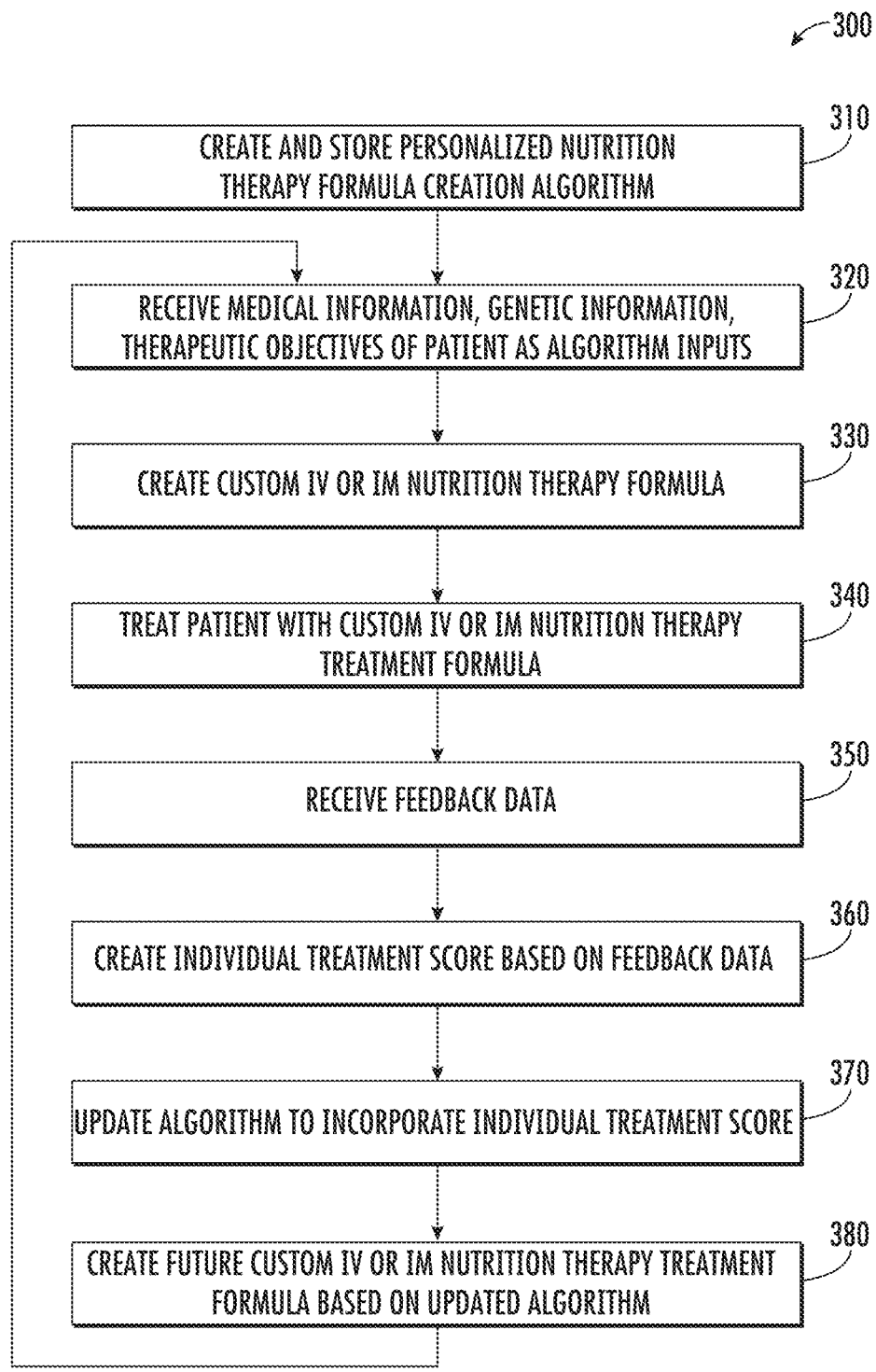
FIG. 7 shows a process flow for creating custom IV or IM nutrition therapy treatment formulas according to some embodiments.

In some embodiments, personalized therapy may be provided through one or more algorithms, as shown, for example, in FIGS. 5-7. In some embodiments, the algorithms may include the process discussed above with respect to FIGS. 1-4. However, other algorithms may also be used.

FIG. 5 illustrates an implementation of a method 2 of providing personalized therapy. As shown, the system may first collect medical data from a customer 10, or the recipient of the personalized therapy. This data may include symptoms 12, medical history 14, blood test results 16, and vitals 18. In some embodiments, the customer 10 may provide the data through an electronic device. For example, the customer 10 may input data into an app run on a smart phone, tablet, or personal computer. Alternatively, a healthcare provider may obtain the data from the customer through medical tests, questioning the customer 10, reviewing health records of customer 10, or through other means (or a combination of these options). The healthcare provider may enter the obtained data into the system (e.g., through an app run on a smart phone, tablet, personal computer, or other electronic device). In some embodiments, data may automatically be received by the system. For example, medical tests may be configured to directly provide results (e.g., blood test results 16, vitals 18, etc.) to the system electronically.

Once the data has been collected, the data may be fed into an algorithm 20. In some embodiments, the algorithm 20 is configured to map the data into a code 30, such as an ICD-11 code or ICD-10 code. The code 30 may represent a condition or type of condition. For example, in the ICD-10 code, an acute upper respiratory infection 32 may be coded as J06.9, fatigue 34 may be coded as R53, and fibromyalgia 36 may be coded as M79.7. The coding may be different in the ICD-11 code.

In some embodiments, these codes 30 may be fed into another algorithm (e.g., recommendation algorithm 40) to determine a personalized nutrition therapy for customer 10. Recommendation algorithm 40 may be based on scientific evidence 42 and feedback 44 already obtained through monitoring past recipients that monitors efficacy of previous treatments. In some embodiments, recommendation algorithm 40 takes into account genetic information of customer 10 in addition to the results from code 30. For example, recommendation algorithm 40 may use scientific evidence 42, monitoring efficacy 44, code 30, and genetic information of customer 10 (e.g., SNP) to determine micronutrients most suited for customer 10.

In some embodiments, recommendation algorithm 40 may be configured to identify an existing product 50, with particular nutritional formulas, that is best suited to meet the nutritional needs of the customer 10. For example, the system may include a number of existing products 50, such as Hydromax IV 51, Ultraviv IV 52, Megaboost IV 53, Vitaglow IV 54, Royal Flush IV 55, Vitamin B12 IM 56, or other IV or IM products 50. Algorithm 40 is configured to evaluate which of the existing products 50 is best suited to provide micronutrients that customer 10 needs in light of the code 30, scientific evidence 42, feedback 44 that monitors efficacy, and genetic information of the customer 10. Alternatively, in some embodiments, a completely new formula may be developed to more effectively meet the nutritional needs of the customer 10. As mentioned, both algorithm 20 and recommendation algorithm 40 may be implemented by a person, or may be automated on a computer or other computing device.

As a specific example, if an end user, which may be a healthcare provider or a patient, inputs a patient's symptoms, conditions, and/or therapeutic objectives into a provider interface, the interface interacts operatively with a processor and associated database to match the symptoms and/or the conditions and/or the therapeutic objectives to a diagnostic ICD-10 code that sits behind a first algorithmic step. For example, as shown in chart 1300 in FIG. 13, if a user enters brain fog/poor concentration, fatigue/low energy, joint pain, muscle ache, nerve pain, pins and needles, and chronic widespread pain as symptoms or conditions, then the diagnostic ICD-10 code may be the code for fibromyalgia.

Once an ICD-10 code has been reached, the system, powered by software, may select an existing formula or create a custom formula (e.g., based on a mapping of the code and/or genetic information to micronutrients). In some embodiments, the system may select an existing formula or create a custom formula based directly on genetic information, symptoms, conditions, and/or therapeutic objectives without determining a code. Over time, there may be less of a need to create a brand new formula because the system will have previously created custom formulas for similar combinations of genetic information (e.g., SNP), symptoms, conditions, and/or therapeutic objectives. Thus, after determining the appropriate formula, the system may consult the database for an existing formula (either a standard formula or a previously made custom formula) that matches the nutritional needs of the patient. Example formulas that may have been created through the processes disclosed herein are provided in chart 1400 shown in FIGS. 14A-14F. If the code and/or genetic information best matches to an existing laboratory tested formulation product based on a scientific library of evidence used to create the formulation products (e.g., the mapping discussed above), then that product will be selected. In some embodiments, the system creates a new custom formula by tweaking an existing formula or by making a new combination of micronutrients (or new amounts of the micronutrients) that are determined to be a match for the patient's information based on the mapping.

Figure 15:
FIG. 15 shows a chart mapping ingredients of a custom formula to fibromyalgia according to some embodiments.

For example, as shown in chart 1500 in FIG. 15, the mapping for fibromyalgia may lead to a custom formula that includes cyanocobalamin, vitamin B5, sodium ascorbate, ergocalciferol, and cholecalciferol. These ingredients may be the identified one or more micronutrients discussed above with respect to FIGS. 1-4. In some embodiments, a specific dosage for each of these ingredients may be provided based on the mapping of genetic information, symptoms, conditions, and/or therapeutic objectives. The formulations may be shared with the end user (e.g., a healthcare provider that will prescribe the custom formula). In some embodiments, the formulation may include a certificate of analysis for the safety of that formulation as an infusion. In some embodiments, the formulation may include documentation on the scientific reasoning for why the ingredients were chosen (e.g., from the database comprising the scored scientific literature references). The healthcare provider may review the custom formula to ensure the safety and appropriateness of prescribing the custom formula to the patient. In some embodiments, a life science team evaluates and establishes which nutrients show improved outcomes in relation to prescribed therapies and feedback from patients, to know which improved outcomes are statistically significant.

Figure 16:
FIG. 16 shows a chart displaying a custom formula to a healthcare provider according to some embodiments.

In some embodiments, the ordinary end user of the interface and software does not see the mapping. Instead, they just input the patient's symptoms, conditions and therapeutic objectives and a formulation displays for the end user to prescribe. For example, the custom formula that has been created may be displayed to a healthcare provider in the format shown in chart 1600 in FIG. 16. For example, a custom formula may include normal saline at 0.9% concentration, along with 4 other ingredients (e.g., micronutrients) that have been selected based on the mapping. In some embodiments, the custom formula may also indicate the correct dosage or volume of each ingredient of the formula. In some embodiments, the custom formula may also indicate the method of delivery (IV or IM).

Figure 17B:
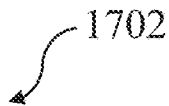
FIG. 17B shows a listing of links between conditions and scientific literature according to some embodiments.

In some embodiments, the scientific library of evidence includes relevant papers behind each ICD-10 code, as shown in FIGS. 17A and 17B. For example, for each of the scientific literature references that was considered for the mapping, there may be a link to the relevant codes, symptoms, genetic information, conditions, and/or therapeutic objectives. In some embodiments, there may also be stored one or more comments on each paper to understand the power of each study. An example of a listing 1700 of each paper with comment(s) is shown in FIG. 17A. An example of the link between literature and codes/micronutrients is shown in chart 1702 in FIG. 17B. As discussed above, the scientific literature references may be scored to determine relevant micronutrients for various combinations of genetic information, symptoms, conditions, and/or therapeutic objectives. As also discussed above, the system evaluates what is the best match based on the level of existing evidence.

Figure 18:
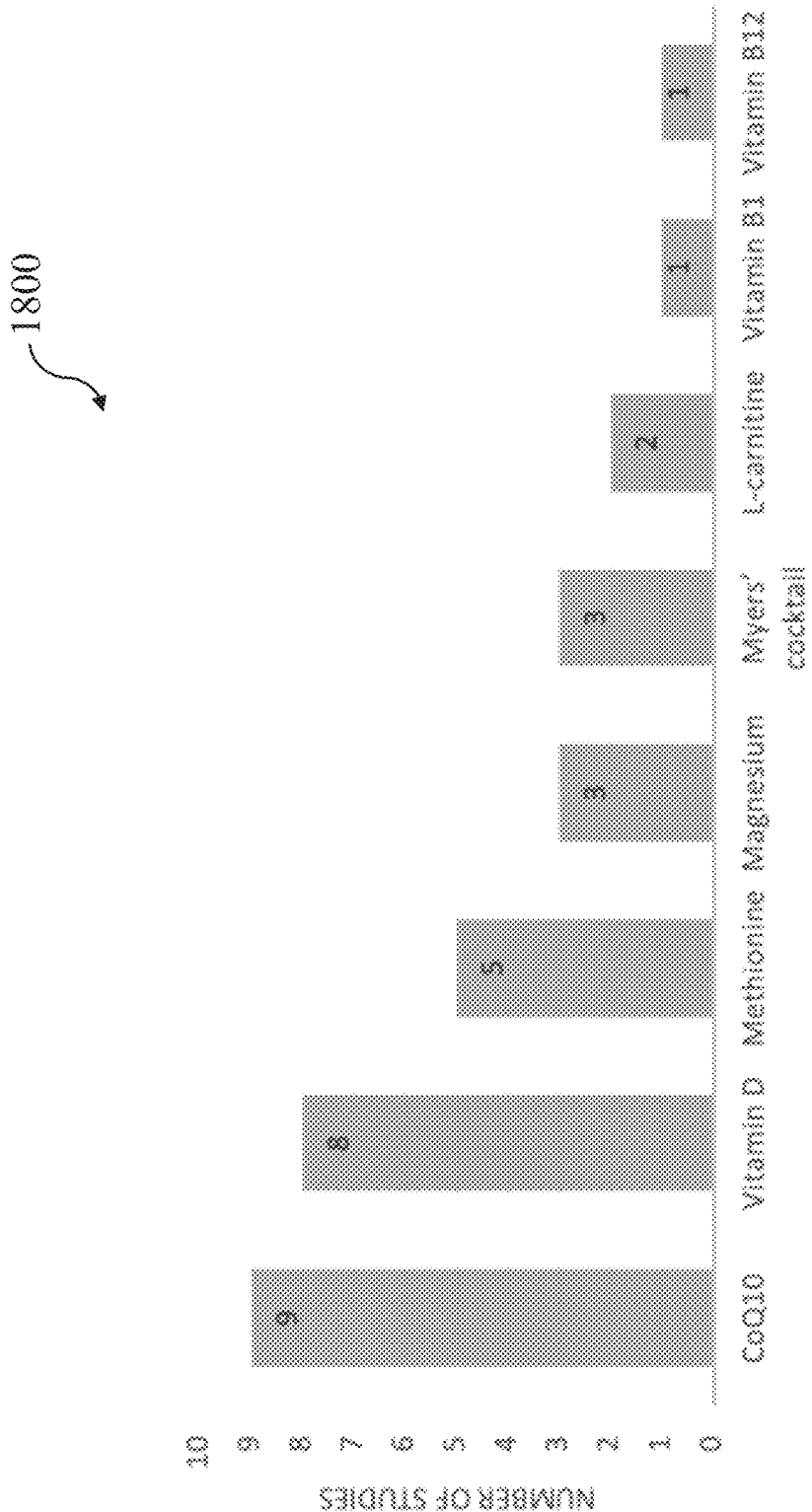
FIG. 18 shows a chart of number of studies finding a link between a micronutrient and ingredients according to some embodiments.
Figure 19:
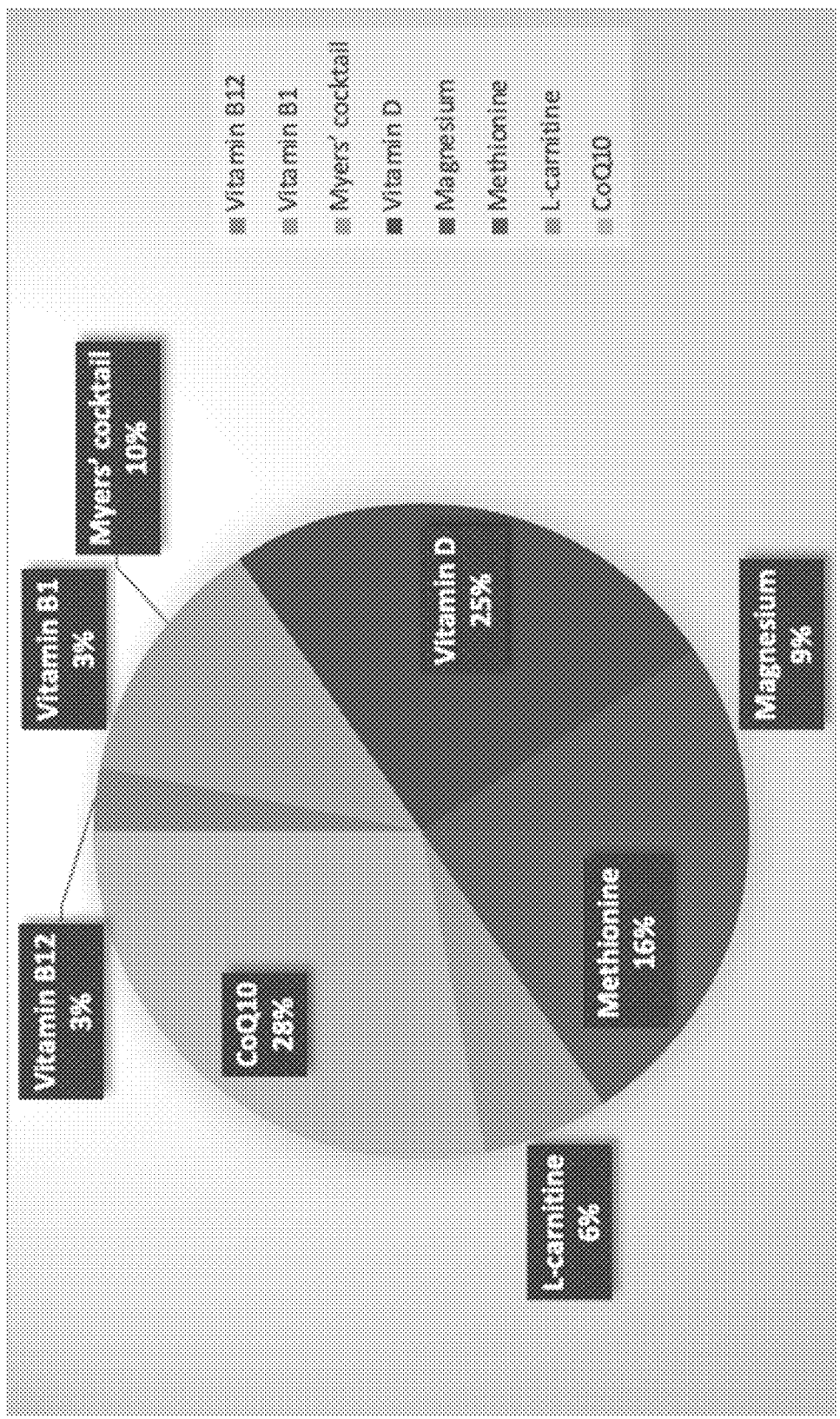
FIG. 19 shows a chart of percentage of studies finding a link between a micronutrient and ingredients according to some embodiments

In some embodiments, the interface of the system and the software may also be configured to visualize the relevant nutrients in several formats. Chart 1800 in FIG. 18 and chart 1900 in FIG. 19 are example formats that illustrate the number of studies (or the percentage of studies) that link a micronutrient to a particular symptom, condition, therapeutic objective, or genetic information.

Figure 20:
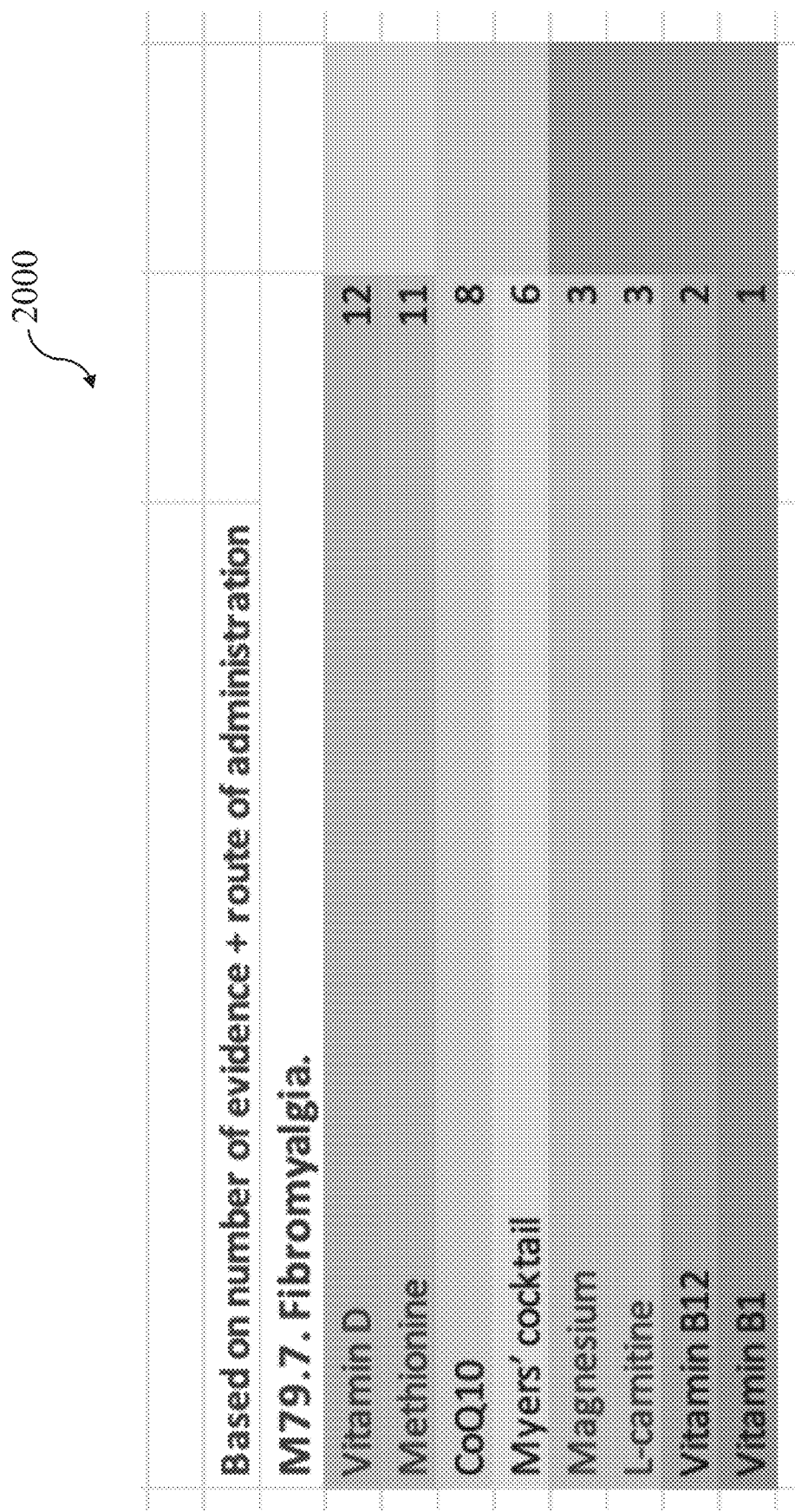
FIG. 20 shows a matching of ingredients to fibromyalgia according to some embodiments.

As discussed above, the scoring may be applied to nutrients based on the number of statistically significant papers, study limitations and relevance of the paper to IV therapy/nutritional therapy. An example of representative matching 2000 is illustrated in FIG. 20 for fibromyalgia.

Another example implementation is provided in FIG. 6, illustrating a method 4 of providing personalized therapy to target a specific disease, such as fibromyalgia, and its symptoms. Fibromyalgia is a disease in which the main symptom is chronic, strongly systemic pain, or, even if partial, widespread chronic pain, the pain being observed not only in muscular tissues but also in the skin. In fibromyalgia, such systemic chronic pain is often not alone and is also accompanied by feelings of fatigue, malaise, depression, anxiety, morning stiffness, muscle stiffness, sleep disturbance or the like. In addition, symptoms such as headache, facial pain, cognitive impairment (lapse of memory, concentration deficit), gastrointestinal complaints (visceral pain, digestive system disturbance, flatulence), frequent urination, diarrhea, constipation, or dysmenorrhea may also occur concomitantly.

As already discussed in the previous example, the medical and genetic data of customer 10 may be collected. In this particular example, the customer 10 presents data indicative of fibromyalgia. Thus, when the data is fed through the algorithm 20, the code 30 results in the code for fibromyalgia. Similar to the previous example, the code 30 is fed into recommendation algorithm 40, which may also take into account the genetic data of customer 10, to arrive at a recommended formula (e.g., a custom formula or an existing formula) based on scientific evidence 42 and feedback 44 that monitors efficacy. In some embodiments, recommendation algorithm 40 may create a custom nutrition therapy treatment formula that includes co-enzyme Q10 (CoQ10), a co-enzyme with a molecular structure of 2,3-dimethoxy-5-methyl-6-decaprenil-1,4-benzoquinone, which may be administered to the customer 10 through IV or IM therapy to treat fibromyalgia and its symptoms. A pharmaceutical composition of CoQ10 may also or alternatively be administered. In some instances, the CoQ10 composition 60 administered may contain CoQ10 and vitamin B12 (as shown in FIG. 6). In some embodiments, recommendation algorithm 40 may output current studies 76 that link the recommended micronutrient ingredients (e.g., CoQ10, Vitamin B12, etc.) to the condition of fibromyalgia.

In some embodiments, at operation 70, outcomes of the treatment may then be measured. For example, outcomes may be measured through blood tests, vitals, and feedback from the customer 10, as well as other means, including those discussed above for FIGS. 1-4. These outcomes can be used at operation 75 to build evidence of what works and what doesn't, which can then be used to improve recommendations to future customers. In other words, the outcomes of each treatment of each customer may contribute to feedback 44 that monitors efficacy. This feedback may be tied to specific medical and genetic data, leading to more personalized results over time.

In some embodiments, a life science team 72 may evaluate the measurements 70 along with other available medical data and genetic data to gain additional insight 82. Additional analysis and/or studies related to the outcomes may improve evidence at operation 80 for what can be adjusted to alter outcomes at operation 85. For example, results from the measurements 70 may be analyzed in connection with medical or genetic data to determine specific dosages of an ingredient or a therapy formula that maximize results for certain situations. Thus, the dosage of the CoQ10 composition 60 used may be determined by the customer's medical data, genetic data, and/or medical history. An example of additional insight 82 is shown in FIG. 6, in which the genetic data of customer 10 may identify a single-nucleotide polymorphism (SNP) for CoQ10 activation. In such an instance, depending on the characteristics of that particular SNP, the dosage of CoQ10 may need to be increased or decreased due to the customer's reaction to CoQ10. Additionally, feedback may be received from the customer 10 regarding the effect of the dosage on the recipient. Based on this feedback and the knowledge concerning the recipient's medical data, medical history, and genetic data, the dosage may be adjusted to better provide the nutritional benefits of the CoQ10.

Although FIG. 6 provides one example of a disease that may be treated through IV or IM therapy (i.e., fibromyalgia), other diseases may also be treated through IV or IM therapy with similar methods of treatment, where different dosages and different substances may be used, but the same method of using genetic data to personalize the treatment is implemented.

FIG. 7 illustrates a method 300 of creating and using a personalized nutrition therapy formula creation algorithm that is updated over time to improve accuracy and personalization of nutrition therapy. At operation 310, a personalized nutrition therapy formula creation algorithm is created. In some embodiments, the algorithm is configured to receive one or more inputs and create a custom IV or IM nutrition therapy treatment formula to treat a patient based on the inputs. The inputs may include medical information, genetic information, and therapeutic objectives, as discussed further below. The algorithm may also output a recommended dosage of the custom IV or IM nutrition therapy formula in addition to creating the formula.

In some embodiments, the algorithm is created based on existing scientific literature. For example, the algorithm may be based on a mapping of medical information, genetic information, and therapeutic objectives to micronutrients, as discussed above with respect to FIGS. 1-4. Thus, the algorithm may include a set of rules, established by existing scientific literature that links micronutrients to various medical information, genetic information, and therapeutic objectives, so that a custom nutrition therapy formula containing the desired micronutrients is created and the most suitable dosage is recommended given a certain set of medical information, genetic information, and therapeutic objectives. Once created, the algorithm may be stored in a database. For example, the algorithm may be stored in a database on a server so that users can run the algorithm on an electronic device in communication with the server.

In some embodiments, at operation 320, medical information, genetic information, and therapeutic objectives of a patient are received as algorithm inputs. A user (e.g., a patient or a healthcare provider) may input only medical information, only genetic information, only therapeutic objectives, or any combination of this information (e.g., medical information, genetic information, and therapeutic objectives) as inputs to the algorithm. In addition, a user may enter a single input under a category or multiple inputs. For example, a user may enter one therapeutic objective or multiple therapeutic objectives.

In some embodiments, the medical information may include blood test results, vital signs (e.g., blood pressure, heart rate, heart rhythm, etc.), medical histories, medical diagnoses, current symptoms, diseases of which the patient is at heightened risk, family history, or other medical information. Medical information may include biodata that is captured and measured through various processes, which may include blood testing, urine sampling (e.g., toxicology screens, etc.), stool sampling, continuous blood glucose monitoring, and imaging/scanning (e.g., ultrasound, etc.). Devices may include blood pressure monitors, heart rate monitors, body hydration monitors, breathalyzers, blood glucose monitors, metabolic devices, pulse oximeters, and wearable devices configured to measure any type of biodata.

In some embodiments, the genetic information comprises genetic test results. The genetic information may comprise a gene, genome, SNP, or other piece of genetic data. In some embodiments, the genetic information comprises epigenetic measurements (e.g., epigenetic clocks, methylation scores, etc.)

A variety of therapeutic objectives may be used as inputs. For example, the therapeutic objectives may comprise health goals, aesthetic goals, or fitness goals. The therapeutic objectives may be to lose weight, to gain weight, to improve fitness level, to improve energy levels, to alter skin tone (to either a darker tone or a lighter tone), to improve skin quality and/or health, to improve hair quality and/or health, to improve mental acuity, to prevent disease, to improve symptoms of an existing illness or disease, to improve sleep quality, to improve longevity/anti-aging, to protect against excessive stress, to protect against toxin exposures (e.g., from pollution, chemicals, alcohol, etc.), to rehydrate, to support immune health, and/or to heal a wound. Other therapeutic objectives may also be used.

In some embodiments, at operation 330, the personalized nutrition therapy formula creation algorithm creates a custom IV or IM nutrition therapy treatment formula based on the medical information, genetic information, and therapeutic objectives of the patient that were received as algorithm inputs. For example, the algorithm may determine ingredients for the custom formula by identifying one or more micronutrients that match the medical information, genetic information, and/or therapeutic objectives. In some embodiments, the custom formula comprises an existing IV or IM nutrition therapy formula (e.g., products 50, as shown in FIG. 5) that is modified by an additional ingredient, which may be a micronutrient identified as a match for the medical information, genetic information, and therapeutic objectives.

In some embodiments, the algorithm identifies a match based on both scientific literature and previous IV or IM nutrition therapy treatments. For example, the database may store individual scores of multiple existing individual scientific literature references relating to the identified micronutrient. These individual scores may be specific to the inputted medical information, genetic information, and therapeutic objectives. The database may also store individual treatment scores of previous IV or IM nutrition therapy treatments that included the identified micronutrient. Again, these scores may be specific to the inputted medical information, genetic information, and therapeutic objectives. For example, the previous treatments may be from earlier patients that had similar medical information, genetic information, and therapeutic objectives. The individual scores of the scientific literature references and the individual treatment scores discussed here may have the same characteristics and be derived in the same way as the scores discussed above with respect to FIGS. 1-4. The algorithm may determine a match when the scores add up to a predetermined threshold.

At operation 340, the patient is treated with the custom IV or IM nutrition therapy treatment formula from operation 330. At operation 350, feedback data about the results of the custom IV or IM nutrition therapy treatment formula on the patient is received. In some embodiments, the feedback data includes feedback about measured bloodwork, epigenetic changes, improvements or declines in symptoms, progress towards reaching therapeutic objectives, vital signs, overall health and fitness, or physical or mental energy.

In some embodiments, at operation 360, an individual treatment score is created based on the feedback data from operation 350. This individual treatment score may relate to the effectiveness of the identified micronutrient with respect to the inputted medical information, genetic information, and therapeutic objectives. In some embodiments, this individual treatment score may be entered electronically into a computer system associated with the database. For example, an electronic device that receives feedback data may automatically determine the individual treatment score and transmit the individual treatment score to the database to be stored (and thus used in future instances of identifying a match when considering similar medical information, genetic information, or therapeutic objectives). As another example, a user, such as a healthcare provider may manually enter an individual treatment score into an electronic device so that it can be stored in the database.

In some embodiments, the algorithm is updated to incorporate the individual treatment score at operation 370. In some embodiments, the algorithm is updated to incorporate new scientific literature references. Thus, the algorithm may account for recent published science. At operation 380, future custom IV or IM nutrition therapy formulas are created based on the updated algorithm. Thus, subsequent patients using the system will have the benefit of feedback from the patient's treatment to more accurately identify micronutrients that are most effective for specific combinations of medical information, genetic information, and therapeutic objectives. The updated personalized nutrition therapy formula creation algorithm is thus configured to create custom IV or IM nutrition therapy treatment formulas that include as ingredients the micronutrients that most closely match patient needs based on all available patient medical information, genetic information, and therapeutic objectives, and most current aggregated feedback based on real patients with similar genes and symptoms.

After operation 380, the process is repeated (beginning at operation 320) for every subsequent patient. This creates a real time feedback loop that automatically applies patient therapy feedback data to the personalized nutrition therapy formula creation algorithm. In this way, all new therapy recommendations include the feedback data from all previous patients who received custom IV or IM nutrition therapy treatment formulas through the algorithm. While the algorithm is originally based on existing scientific references, the feedback from actual treatments is constantly used to update the algorithm. In some embodiments, new scientific references may also be scored and used to update the algorithm. The algorithm will therefore be more up to date than existing published science alone.

In some embodiments, the patient and the subsequent patients (or at least some of the patient and the subsequent patients) are positioned geographically remote from each other.

Figure 8:
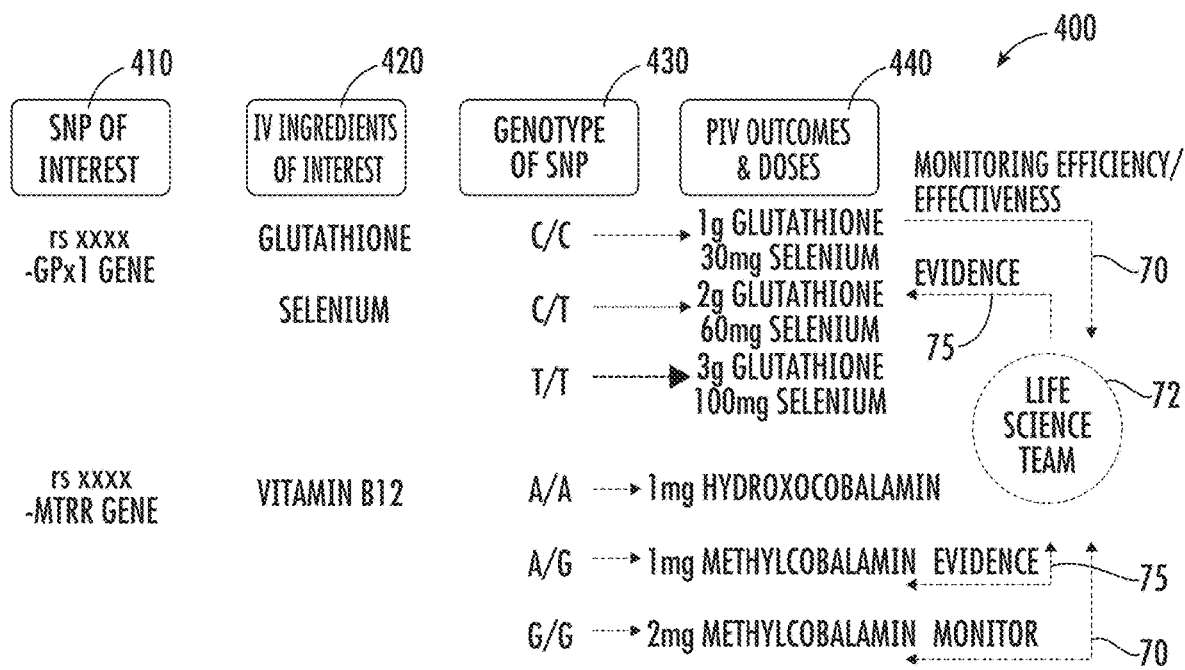
FIG. 8 shows a schematic representing a nutritional database according to some embodiments.

As explained above, genetics can influence the proper nutrition for a particular recipient. For example, a single-nucleotide polymorphism (SNP) in genetic material can, among other things, indicate differences in susceptibility to various diseases. As such, SNPs of different types lead to different desired doses as part of a therapy treatment. As shown in FIG. 8, the nutritional database may incorporate this information to point to particular effective nutrients. FIG. 8 presents a schematic 400 that represents a portion of the nutritional database, including SNPs 410 of interest, IV ingredients 420 of interest for the SNPs 410, genotypes 430 of the SNPs 410, and associated outcomes and doses 440 of the IV ingredients 420 based on the genotypes 430. For example, IV ingredients 410 (i.e., micronutrients) such as glutathione and selenium are of particular interest for the GPx1 gene SNP 410. Depending on the genotype 430 of the SNP 410, different amounts of glutathione and selenium are recommended. Similarly, vitamin B12 is relevant to the MTRR gene SNP 410, and depending on the genotype 430, different amounts of hydroxocobalamin or methylcobalamin may be recommended. Thus, genetic testing may form an important part of the personalized therapy disclosed herein.

As an illustrative example, glutathione and selenium are both important for immune system health. Glutathione performs an antioxidant function and may be involved in immune stimulation and detoxification of xenobiotics (see Pastore et al. 2003. Clinica Chimica Acta 333: 19-39). In general, it is known that glutathione synthesis genes are essential for survival, and organisms deficient in these genes are less resistant to oxidative stress and various harmful substances. In addition, there is a report that various human diseases are associated with a decrease in glutathione concentration in body (Wu et al. 2004. J. Nutr. 134: 489-492). Similarly, selenium is an antioxidant that helps lower oxidative stress in the body, reduces inflammation, and enhances immunity. As shown in FIG. 8, a method for treating a glutathione deficiency or a selenium deficiency in a subject may comprise administering either glutathione or selenium, or a pharmaceutical composition thereof. The glutathione or selenium may be administered through IV therapy, and the dosage 440 may be dependent on a genotype 430 of the GPx1 gene SNP 410 of the subject. In this way, personalizing to the genetic data of the recipient improves the effect of the IV treatment. For example, as shown in FIG. 8, if the genotype 430 of the GPx1 gene SNP 410 is C/C, the glutathione dosage 440 may be 1 g, if the genotype 430 of the GPx1 gene SNP 410 is C/T, the glutathione dosage 440 may be 2 g, and if the genotype 430 of the GPx1 gene SNP 410 is T/T, the glutathione dosage 440 may be 3 g. Similarly, if the genotype 430 of the GPx1 gene SNP 410 is C/C, the selenium dosage 440 may be 30 mg, if the genotype 430 of the GPx1 gene SNP 410 is C/T, the selenium dosage 440 may be 60 mg, and if the genotype 430 of the GPx1 gene SNP 410 is T/T, the selenium dosage 440 may be 100 mg.

As another illustrative example, vitamin B12 is a micronutrient that helps keep the body's blood and nerve cells healthy and helps make DNA. Vitamin B12 may also help prevent anemia, which causes tiredness and fatigue. A method of treating a vitamin B12 deficiency in a subject may comprise administering at least one of hydroxocobalamin and methylcobalamin, or a pharmaceutical composition thereof, through IV or IM therapy. The dosage 440 may be dependent on a genotype 430 of the MTRR gene SNP 410 of the subject. Thus, again, personalizing the dosage 440 based on the genetic data of the recipient improves the effect of the IV treatment. For example, if the genotype 430 of the MTRR gene SNP 410 of the subject is A/A, the dosage 440 may be 1 mg of hydroxocobalamin, if the genotype 430 of the MTRR gene SNP 410 of the subject is A/G, the dosage 440 may be 1 mg of methylcobalamin, and if the genotype 430 of the MTRR gene SNP 410 of the subject is G/G, the dosage 440 may be 2 mg of methylcobalamin.

In some embodiments, feedback is received about the effectiveness of the dosage 440 for each treatment of a patient, similar to the feedback discussed above. Thus, over time, the nutritional database 400 may be updated to improve accuracy and personalization. This may be done using the processes discussed with respect to FIGS. 1-4 and 7. In some embodiments, a life science team 72 may monitor efficiency/effectiveness of the dosages 440 at operation 70. In addition, the life science team 72 may compile and/or develop evidence of what works and what doesn't at operation 75 to improve recommendations of dosages 440 to future customers.

Additional example ingredients may be selected and/or formulas created based on the genes, SNPs, and genotypes of the recipient. In addition, the recommended dosages for various ingredients may vary based on the genotype of the recipient. For example, in relation to the GSTP1 gene, if the recipient has the A/A genotype, the recipient may receive 0 g of glutathione and 300 mg of NAC. If the recipient has the A/G genotype, the recipient may receive 1 g of glutathione and 400 mg of NAC. Lastly, if the recipient has the G/G genotype, the recipient may receive 2 g of glutathione and 500 mg of NAC. Thus, the genetic data of the recipient influences the recommended dosage 540. In addition, the medical data of the recipient can influence the recommended dosage (as discussed above). For example, again in relation to the GSTP1 gene, if the recipient has exposure to polycyclic aromatic hydrocarbons (PAH), the dosage of glutathione may be increased by 1 g.

Figures 9, 10:
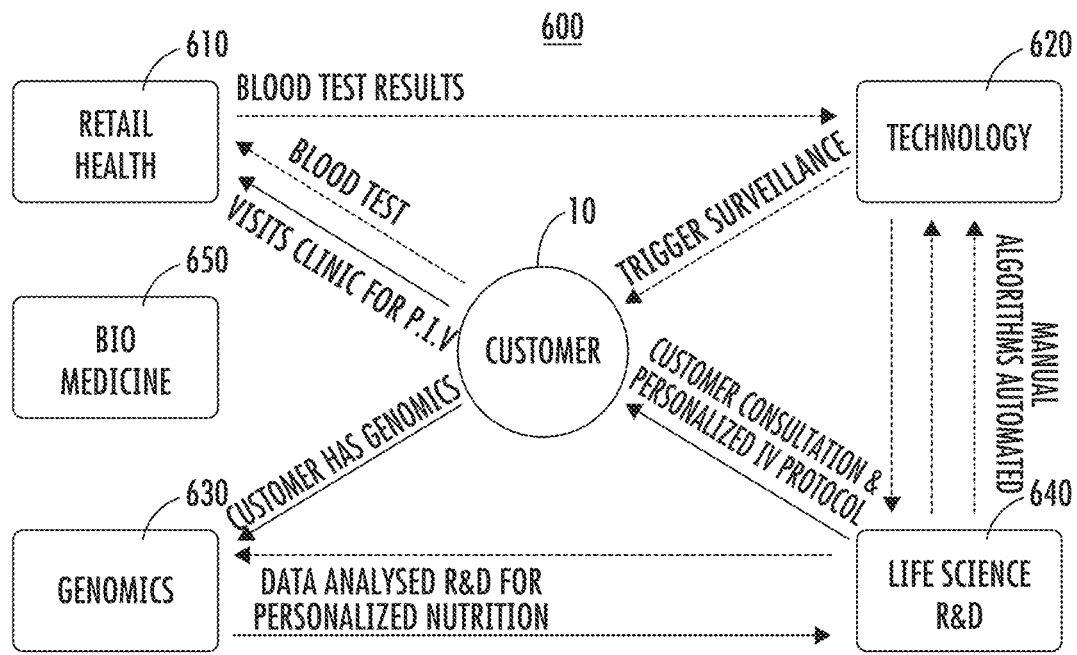
FIG. 9 shows a schematic representing a holistic approach to implementing a genetically personalized IV or IM nutrition therapy according to some embodiments.
FIG. 10 shows a genetically personalized nutrition therapy system according to some embodiments.

An individual's health and nutritional needs are influenced by a variety of factors that are understood through numerous fields of study. For example, pharmacology, genetics, nutrigenomics, dietetics, clinical medicine, biomedicine, molecular biology, and epigenetics all contribute to understanding nutritional needs and how to meet them. In addition, other fields such as statistics and technology are involved in the methods described herein. For this reason, a holistic approach to implementing the personalized therapy systems and methods is beneficial. FIG. 9 illustrates an example of how different areas may be involved in the methods disclosed herein. Specifically, schematic 600 in FIG. 9 illustrates various interactions between the areas of retail health 610, technology 620, genomics 630, and life science research and development 640, to provide bio medicine 650 to customer 10. Though not all implementations involve automated steps, including technology 620 may increase the accessibility and accuracy of personalized therapy.

In some embodiments, as shown, for example, in FIG. 10, a system 700 comprises a number of electronic devices (e.g., a first user's electronic device 710 and a second user's electronic device 720), a network 730, and a genetically personalized therapy system 740. The genetically personalized therapy system 740 disclosed herein may be implemented with a computer or other electronic device. For example, as shown in FIG. 10, the genetically personalized therapy system 740 may comprise a processor 750 and a storage 760. In some embodiments, the processor 750 is communicatively coupled to network 730 and the storage 760. The electronic devices 710, 720 are also communicatively coupled to network 730, allowing users (such as first and second user) to access the genetically personalized therapy system 740.

In some embodiments, the storage 760 may comprise a user library 770 with a plurality of user profiles including a first user profile 772 and a second user profile 776. The user profiles 772, 776 may correspond to each recipient of the personalized therapy disclosed above (e.g., the first user and the second user associated with electronic devices 710, 720). Each user profile may include the genetic data of the user, the medical data of the user, the medical history of the user, and the personal therapeutic objectives of the user. For example, first user profile 772 includes the genetic and medical data 774 of the first user and second user profile 776 includes the genetic and medical data 778 of the second user. In some embodiments, users may enter or update this data via their electronic devices 710, 720. In some embodiments, other users (e.g., healthcare providers) may gain access to another user's profile to enter or update genetic and medical data. For example, the first user's healthcare provider may gain access to first user profile 772 to update genetic and medical data 774.

The storage 760 may also comprise the nutritional database 780, including the typical nutrient requirements 782 of the human body and the modifications 784 that occur to these requirements based on the genetic data of the user, the medical data of the user, and the medical history of the user.

In some embodiments, the processor 750 comprises a number of modules to perform various actions. For example, the processor 750 may comprise a profile creation module 752, a genetic testing module 754, a formula creation module 756, and/or a database adjustment module 758. The modules may work together. The profile creation module 752 may assist a new user creating a profile from their electronic device. As part of this module, the processor 750 may be configured to receive the genetic data, the medical data, the medical history, and the personal therapeutic objectives of the user. For example, first user may create a profile with the first user's electronic device 710. As the first user enters data on electronic device 710, electronic device 710 may transmit the data over network 730 to genetically personalized therapy system 740. Processor 750 (through its profile creation module 752) may receive the data, create a new user profile (i.e., first user profile 772), and store the data 774 in the first user profile 772.

The genetic testing module 754 may assist a user in determining genetic data. For example, the processor may send instructions to a user's electronic device (first user's electronic device 710) on how to use a genetic testing kit. In some embodiments, the user enters results of the genetic test onto the electronic device 710, which is then transmitted to genetically personalized therapy system 740. Processor 750 (through its genetic testing module 754) may then add the results of the genetic testing to the user's profile. In some embodiments, the genetic testing kit may send results directly to genetically personalized therapy system 740 over network 730. The genetic testing module 754 may operate as part of profile creation module 752 or it may be used later on after a profile has already been created.

Formula creation module 756 may create a custom IV or IM nutrition therapy treatment formula for a user. For example, the formula creation module 756 may be configured to analyze the genetic data, medical data, medical history, and personal therapeutic objectives of the user stored in a user profile (e.g., first user profile 772) using the nutritional database 780 to determine the nutritional needs of the user, and create a formula (e.g., determine which ingredients should be included and their amounts) based on the nutritional needs of the user. Formula creation module 756 may follow the processes discussed above with respect to FIGS. 1-4 and 7.

Database adjustment module 758 may operate to update the nutritional database 780 to improve accuracy and personalization of the system 740. In some embodiments, after the user has received the custom formula via IV therapy, processor 750 (through its database adjustment module 758) may receive feedback from the user regarding the effect of the formula. The feedback may be received via the user's electronic device (e.g., first user's electronic device 710) over network 730. The feedback may also be received via another user, such as the first user's healthcare provider. The database adjustment module 758 is configured to adjust the nutritional database 780 based on the feedback from the user and the genetic data, medical data and medical history of the user stored in the user profile. Database adjustment module 758 may follow the processes discussed above with respect to FIGS. 1-4 and 7.

Figure 11:
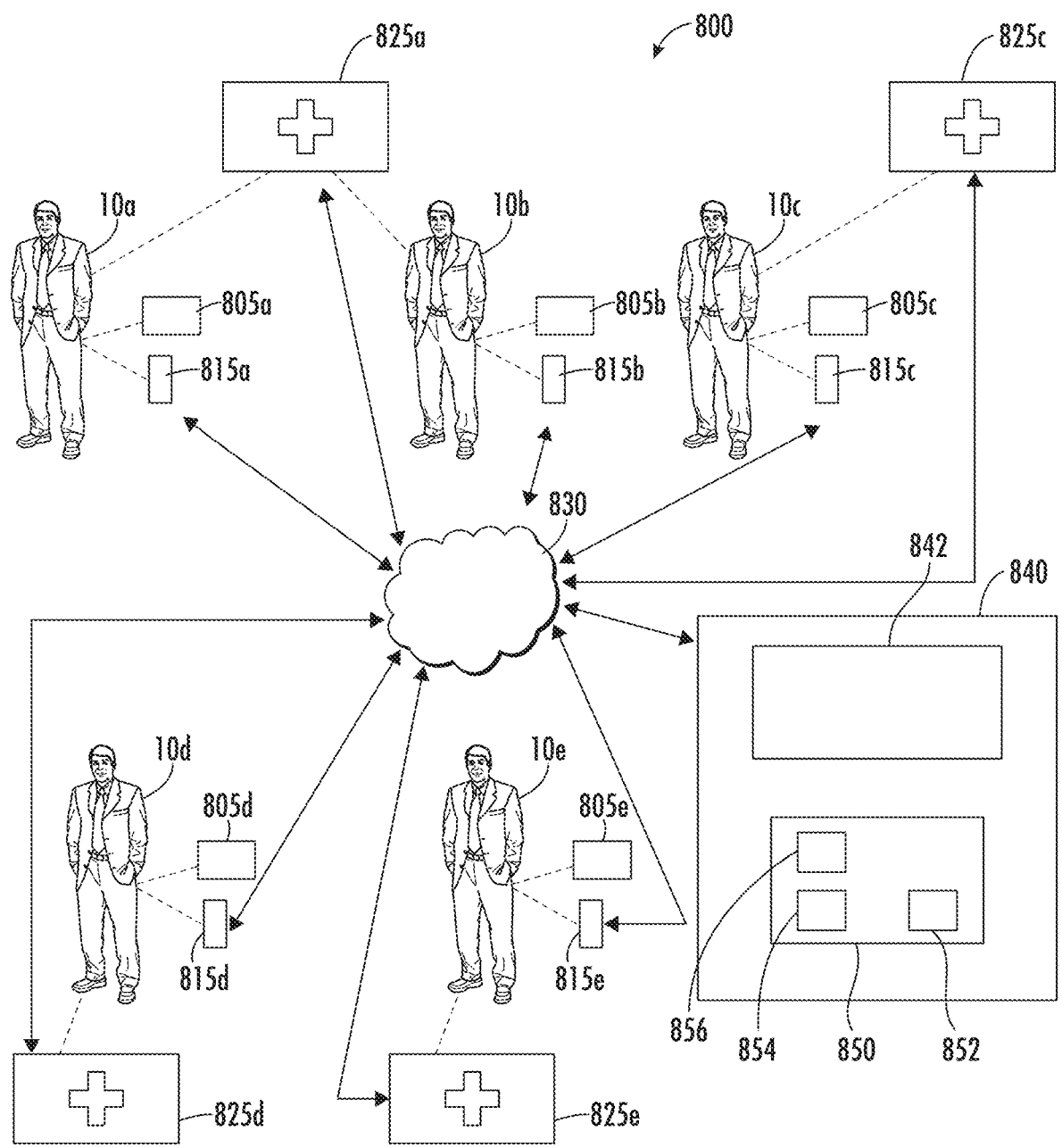
FIG. 11 shows a genetically personalized nutrition therapy system according to some embodiments.

As noted above, the systems disclosed herein benefit from the real-time feedback of how effective each treatment is for multiple recipients in various geographic locations, combined with the genetic and medical data of the recipients. A system 800 illustrating this feature is shown, for example, in FIG. 11. FIG. 11 shows five customers 10a, 10b, 10c, 10d, 10e to illustrate the concept of multiple patients in multiple geographic locations, but in practice there may be many more customers in many more locations (e.g., a worldwide group of customers with locations around the world). In some embodiments, system 800 comprises a plurality of genetic testing kits (e.g., genetic testing kits 805a, 805b, 805c, 805d, 805e), a plurality of electronic devices (e.g., electronic devices 815a, 815b, 815c, 815d, 815e), a network 830, and a server 840.

In some embodiments, each genetic testing kit 805a, 805b, 805c, 805d, 805e is configured to determine genetic information of one of the patients or customers 10a, 10b, 10c 10d, 10e. Dotted lines in FIG. 11 show a connection between each of the genetic testing kit 805a, 805b, 805c, 805d, 805e and respective patients 10a, 10b, 10c, 10d, 10e. The genetic testing kits 805a, 805b, 805c, 805d, 805e may be self-administered or they may be administered by a healthcare provider (e.g., healthcare provider 825a, 825c, 825d, 825e).

In some embodiments, each electronic device 815a, 815b, 815c, 815d, 815e is configured to receive the genetic information of one of the patients 10a, 10b, 10c, 10d, 10e. Dotted lines in FIG. 11 show a connection between each electronic device 815a, 815b, 815c, 815d, 815e and respective patients 10a, 10b, 10c, 10d, 10e. In some embodiments, genetic testing kits 805a, 805b, 805c, 805d, 805e are configured to send genetic test results directly to electronic devices 815a, 815b, 815c, 815d, 815e. Alternatively, patient 10a, 10b, 10c, 10d, 10e may input the genetic information from the genetic test results into electronic devices electronic device 815a, 815b, 815c, 815d, 815e. In some embodiments, each electronic device 815a, 815b, 815c, 815d, 815e is also configured to receive medical information and/or therapeutic objectives of one of the patients 10a, 10b, 10c, 10d, 10e. Electronic devices 815a, 815b, 815c, 815d, 815e may be smartphones, tablets, personal computers, or other electronic devices. Each electronic device 815a, 815b, 815c, 815d, 815e is communicatively coupled with network 830, thus providing electronic devices 815a, 815b, 815c, 815d, 815e access to server 840, which is also communicatively coupled with network 830.

As illustrated in FIG. 11, each patient 10a, 10b, 10c, 10d, 10e may go to a healthcare provider 825a, 825c, 825d, 825e (i.e., a location providing IV or IM nutrition therapies). Dotted lines in FIG. 11 between patients and healthcare providers illustrate a healthcare provider to which a patient goes. Patients may go to the same healthcare provider or a different healthcare provider. For example, patients 10a and 10b may both go to healthcare provider 825a, while patients 10c, 10d, 10e may go to different healthcare providers 825c, 825d, 825e. Thus, patients 10a, 10b, 10c, 10d, 10e may be positioned geographically remote from each other. A single patient may also go to different healthcare providers or locations at different times. In some embodiments, healthcare providers 825a, 825c, 825d, 825e may be communicatively coupled with network 830 through their own electronic devices, allowing the healthcare providers to access server 840 and input information with respect to patients receiving IV or IM therapy at their location.

In some embodiments, server 840 comprises a processor 842 and a database 850. Processor 842 may have the same features of processor 750 discussed above. In some embodiments, database 850 stores a personalized nutrition therapy formula creation algorithm 852, which may have the same features as nutritional database 780. In some embodiments, algorithm 852 may operate the same as the algorithm discussed above with respect to FIG. 7. Database 850 may also store individual scores 854 of a plurality of individual scientific literature references and/or individual treatment scores 856 of previous IV or IM nutrition therapy treatments.

In some embodiments, server 840 is configured to wirelessly receive (e.g., over network 830 from electronic devices 815a, 815b, 815c, 815d, 815e) the genetic information, medical information and therapeutic objectives of each of the patients 10a, 10b, 10c, 10d, 10e. For each patient, the server 840 may be configured to output to a respective electronic device 815a, 815b, 815c, 815d, 815e a custom IV or IM nutrition therapy treatment formula for the patient 10a, 10b, 10c, 10d, 10e from the algorithm 852 based on the genetic information, medical information, and therapeutic objectives for each patient. In some embodiments, the ingredients of the custom intravenous or intramuscular nutrition therapy formula comprise one or more micronutrients identified by the personalized nutrition therapy formula creation algorithm 852 as a match for the medical information, genetic information, and therapeutic objectives of the patient. The micronutrient(s) is/are identified by the personalized nutrition therapy formula creation algorithm as a match for the medical information, genetic information, and therapeutic objectives of the patient based on individual scores 854 stored in the database of a plurality of existing individual scientific literature references relating to the micronutrient(s) and individual treatment scores 856 stored in the database of previous IV or IM nutrition therapy treatments comprising the micronutrient(s).

In some embodiments, the server 840 may be configured to output the custom formula to the respective healthcare provider 825a, 825c, 825d, 825e (e.g., via their own electronic devices) instead of the respective patient's electronic device 815a, 815b, 815c, 815d, 815e. The healthcare provider 825a, 825c, 825d, 825e may evaluate the custom formula to ensure safety of prescribing the custom formula to the patient 10a, 10b, 10c, 10d, 10e. The healthcare provider 825a, 825c, 825d, 825e may then prescribe the custom formula (and potentially make a batch of the custom formula and/or administer it to the patient 10a, 10b, 10c, 10d, 10e).

In some embodiments, server 840 is configured to receive feedback data about results of the custom formula on each patient 10a, 10b, 10c, 10d, 10e after they have been treated. This feedback may be provided from either the patients via the electronic devices 815a, 815b, 815c, 815d, 815e or the healthcare providers 825a, 825c, 825d, 825e via their own electronic devices. The feedback data may include feedback about measured bloodwork, epigenetic changes, improvements or declines in symptoms, progress towards reaching therapeutic objectives, vital signs, overall health and fitness, or physical or mental energy.

In some embodiments, the server 840 is configured to create an individual treatment score 856 based on the feedback data for each patient. Like the earlier individual treatment scores 856, this individual treatment score 856 may be stored in database 850. In some embodiments, the server 840 is configured to update algorithm 852 to incorporate the individual treatment score 856 so that subsequent patients benefit from the feedback. For example, an individual treatment score 856 for patient 10a may be used to update algorithm 852 so that when patient 10e receives treatment at a later time, the algorithm accounts for feedback from patient 10a's treatment. This is particularly beneficial when a subsequent patient has similar genetic data, medical data, and/or therapeutic objectives as an earlier patient. Thus, server 840 is configured to create future custom IV or IM nutrition therapy treatment formulas based on the updated personalized nutrition therapy formula creation algorithm 852, wherein the updated personalized nutrition therapy formula creation algorithm 852 is configured to create custom formulas that include as ingredients the micronutrients that most closely match patient needs based on all available patient medical information, genetic information, and therapeutic objectives, and most current aggregated feedback based on real patients with similar genes and symptoms.

In some embodiments, the methods and systems disclosed herein may account for other factors, such as the location of a patient, or the cost of a nutrition therapy. For example, if a user's electronic device is equipped with a GPS monitor (or other location monitor), the system may identify a region (e.g., country) where the user is located. If a certain micronutrient or IV/IM nutrition therapy is not available in that location for whatever reason (e.g., due to regulations, supply chain issues, etc.), the system may create a custom formula with the next best micronutrient or nutrition therapy. As another example, if the most effective treatment is costly and only slightly better than a less expensive alternative, the system may give the user different options of treatments.

Figure 12:
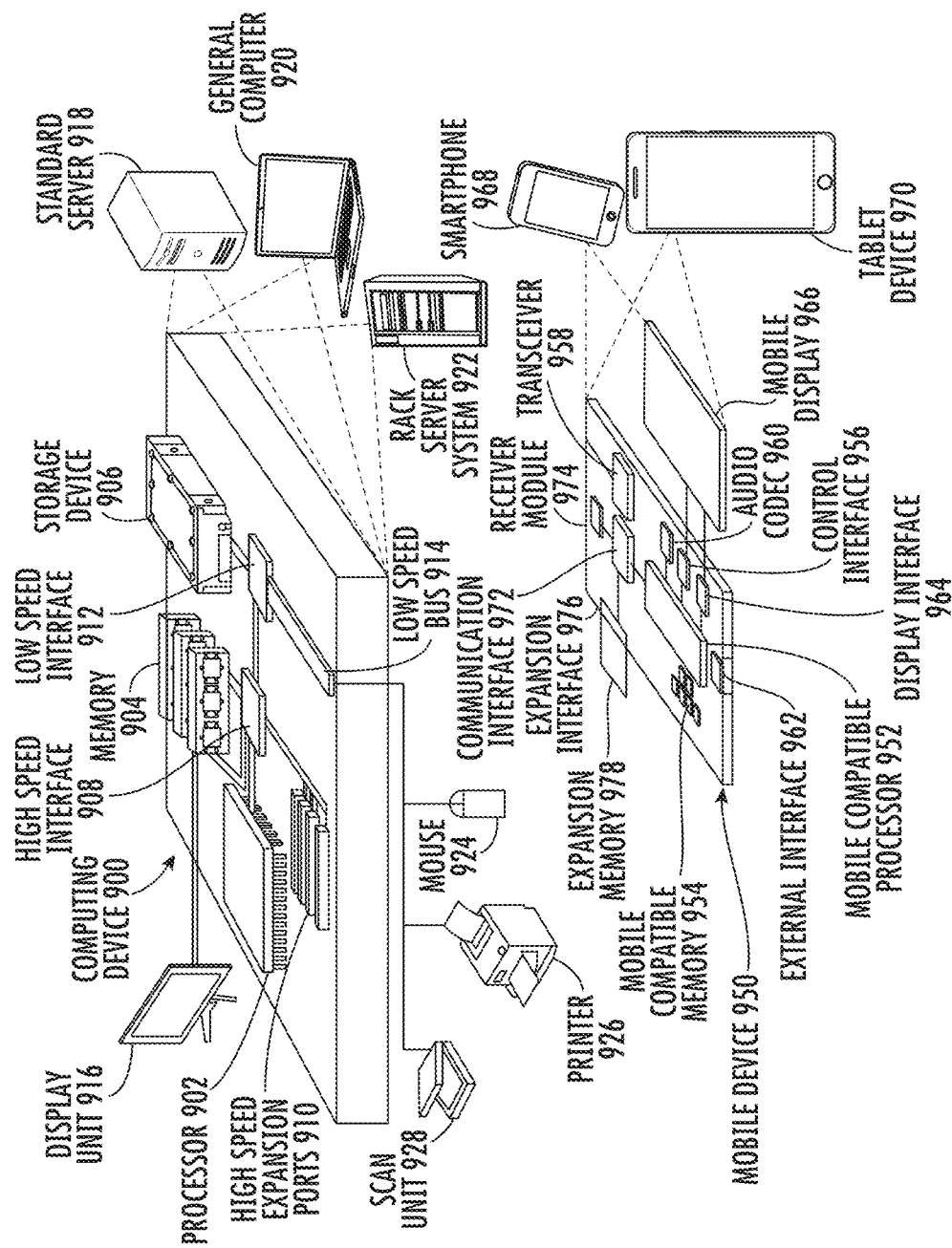
FIG. 12 shows a schematic diagram of computing devices that can be used to perform or implement the embodiments disclosed herein.

As discussed above, the genetically personalized therapy systems and methods disclosed herein may be partially or fully implemented with a computer through software running on or associated with the computer, or an application accessible by the computer or some other electronic device. As one example, FIG. 12 is a schematic diagram of specific computing device 900 and a specific mobile computing device 950 that can be used to perform and/or implement any of the embodiments disclosed herein.

The specific computing device 900 may represent various forms of digital computers, such as laptops, desktops, workstations, personal digital assistants, servers, blade servers, mainframes, and/or other appropriate computers. The specific mobile computing device 950 may represent various forms of mobile devices, such as smartphones, camera phones, personal digital assistants, cellular telephones, and other similar mobile devices. The components shown here, their connections, couples, and relationships, and their functions, are meant to be exemplary only, and are not meant to limit the embodiments described and/or claimed, according to one embodiment.

The specific computing device 900 may include a processor 902, a memory 904, a storage device 906, a high-speed interface 908 coupled to the memory 904 and a plurality of high-speed expansion ports 910, and a low-speed interface 912 coupled to a low-speed bus 914 and a storage device 906. In one embodiment, each of the components heretofore may be inter-coupled using various buses, and may be mounted on a common motherboard and/or in other manners as appropriate. The processor 902 may process instructions for execution in the specific computing device 900, including instructions stored in the memory 904 and/or on the storage device 906 to display a graphical information for a GUI on an external input/output device, such as a display unit 916 coupled to the high-speed interface 908, according to one embodiment.

In other embodiments, multiple processors and/or multiple buses may be used, as appropriate, along with multiple memories and/or types of memory. Also, a plurality of specific computing devices 900 may be coupled with, with each device providing portions of the necessary operations (e.g., as a server bank, a group of blade servers, and/or a multi-processor system).

The memory 904 may be coupled to the specific computing device 900. In one embodiment, the memory 904 may be a volatile memory. In another embodiment, the memory 904 may be a non-volatile memory. The memory 904 may also be another form of computer-readable medium, such as a magnetic and/or an optical disk. The storage device 906 may be capable of providing mass storage for the specific computing device 900. In one embodiment, the storage device 906 may be a floppy disk device, a hard disk device, an optical disk device, a tape device, a flash memory and/or other similar solid state memory device. In another embodiment, the storage device 906 may be an array of the devices in a computer-readable medium previously mentioned heretofore, including devices in a storage area network and/or other configurations.

A computer program may be comprised of instructions that, when executed, perform one or more methods, such as those described above. The instructions may be stored in the memory 904, the storage device 906, a memory coupled to the processor 902, and/or a propagated signal.

The high-speed interface 908 may manage bandwidth-intensive operations for the specific computing device 900, while the low-speed interface 912 may manage lower bandwidth-intensive operations. Such allocation of functions is exemplary only. In one embodiment, the high-speed interface 908 may be coupled to the memory 904, the display unit 916 (e.g., through a graphics processor and/or an accelerator), and to the plurality of high-speed expansion ports 910, which may accept various expansion cards.

In the embodiment, the low-speed interface 912 may be coupled to the storage device 906 and the low-speed bus 914. The low-speed bus 914 may be comprised of a wired and/or wireless communication port (e.g., a Universal Serial Bus ("USB"), a Bluetooth® port, an Ethernet port, and/or a wireless Ethernet port). The low-speed bus 914 may also be coupled to the scan unit 928, a printer 926, a keyboard, a mouse 924, and a networking device (e.g., a switch and/or a router) through a network adapter.

The specific computing device 900 may be implemented in a number of different forms, as shown in the figure. In one embodiment, the specific computing device 900 may be implemented as a standard server 918 and/or a group of such servers. In another embodiment, the specific computing device 900 may be implemented as part of a rack server system 922. In yet another embodiment, the specific computing device 900 may be implemented as a general computer 920 such as a laptop or desktop computer. Alternatively, a component from the specific computing device 900 may be combined with another component in a specific mobile computing device 950. In one or more embodiments, an entire system may be made up of a plurality of specific computing device 900 and/or a plurality of specific computing device 900 coupled to a plurality of specific mobile computing device 950.

In one embodiment, the specific mobile computing device 950 may include a mobile compatible processor 952, a mobile compatible memory 954, and an input/output device such as a mobile display 966, a communication interface 972, and a transceiver 958, among other components. The specific mobile computing device 950 may also be provided with a storage device, such as a microdrive or other device, to provide additional storage. In one embodiment, the components indicated heretofore are inter-coupled using various buses, and several of the components may be mounted on a common motherboard.

The mobile compatible processor 952 may execute instructions in the specific mobile computing device 950, including instructions stored in the mobile compatible memory 954. The mobile compatible processor 952 may be implemented as a chipset of chips that include separate and multiple analog and digital processors. The mobile compatible processor 952 may provide, for example, for coordination of the other components of the specific mobile computing device 950, such as control of user interfaces, applications run by the specific mobile computing device 950, and wireless communication by the specific mobile computing device 950.

The mobile compatible processor 952 may communicate with a user through the control interface 956 and the display interface 964 coupled to a mobile display 966. In one embodiment, the mobile display 966 may be a Thin-Film-Transistor Liquid Crystal Display ("TFT LCD"), an Organic Light Emitting Diode ("OLED") display, and another appropriate display technology. The display interface 964 may comprise appropriate circuitry for driving the mobile display 966 to present graphical and other information to a user. The control interface 956 may receive commands from a user and convert them for submission to the mobile compatible processor 952.

In addition, an external interface 962 may be in communication with the mobile compatible processor 952, so as to enable near area communication of the specific mobile computing device 950 with other devices. External interface 962 may provide, for example, for wired communication in some embodiments, or for wireless communication in other embodiments, and multiple interfaces may also be used.

The mobile compatible memory 954 may be coupled to the specific mobile computing device 950. The mobile compatible memory 954 may be implemented as a volatile memory and a non-volatile memory. The expansion memory 978 may also be coupled to the specific mobile computing device 950 through the expansion interface 976, which may comprise, for example, a Single In Line Memory Module ("SIMM") card interface. The expansion memory 978 may provide extra storage space for the specific mobile computing device 950, or may also store an application or other information for the specific mobile computing device 950.

Specifically, the expansion memory 978 may comprise instructions to carry out the processes described above. The expansion memory 978 may also comprise secure information. For example, the expansion memory 978 may be provided as a security module for the specific mobile computing device 950, and may be programmed with instructions that permit secure use of the specific mobile computing device 950. In addition, a secure application may be provided on the SIMM card, along with additional information, such as placing identifying information on the SIMM card in a non-hackable manner.

The mobile compatible memory may include a volatile memory (e.g., a flash memory) and a non-volatile memory (e.g., a non-volatile random-access memory ("NVRAM")). In one embodiment, a computer program comprises a set of instructions that, when executed, perform one or more methods. The set of instructions may be stored on the mobile compatible memory 954, the expansion memory 978, a memory coupled to the mobile compatible processor 952, and a propagated signal that may be received, for example, over the transceiver 958 and/or the external interface 962.

The specific mobile computing device 950 may communicate wirelessly through the communication interface 972, which may be comprised of a digital signal processing circuitry. The communication interface 972 may provide for communications using various modes and/or protocols, such as a Global System for Mobile Communications ("GSM") protocol, a Short Message Service ("SMS") protocol, an Enhanced Messaging System ("EMS") protocol, a Multimedia Messaging Service ("MMS") protocol, a Code Division Multiple Access ("CDMA") protocol, Time Division Multiple Access ("TDMA") protocol, a Personal Digital Cellular ("PDC") protocol, a Wideband Code Division Multiple Access ("WCDMA") protocol, a CDMA2000 protocol, and a General Packet Radio Service ("GPRS") protocol.

Such communication may occur, for example, through the transceiver 958 (e.g., radio-frequency transceiver). In addition, short-range communication may occur, such as using a Bluetooth®, Wi-Fi, and/or other such transceiver. In addition, a GPS ("Global Positioning System") receiver module 974 may provide additional navigation-related and location-related wireless data to the specific mobile computing device 950, which may be used as appropriate by a software application running on the specific mobile computing device 950.

The specific mobile computing device 950 may also communicate audibly using an audio codec 960, which may receive spoken information from a user and convert it to usable digital information. The audio codec 960 may likewise generate audible sound for a user, such as through a speaker (e.g., in a handset smartphone of the specific mobile computing device 950). Such a sound may comprise a sound from a voice telephone call, a recorded sound (e.g., a voice message, a music files, etc.) and may also include a sound generated by an application operating on the specific mobile computing device 950.

The specific mobile computing device 950 may be implemented in a number of different forms, as shown in the figure. In one embodiment, the specific mobile computing device 950 may be implemented as a smartphone 968. In another embodiment, the specific mobile computing device 950 may be implemented as a personal digital assistant ("PDA"). In yet another embodiment, the specific mobile computing device, 950 may be implemented as a tablet device 970.

Various embodiments of the systems and techniques described here can be realized in a digital electronic circuitry, an integrated circuitry, a specially designed application specific integrated circuits ("ASICs"), a piece of computer hardware, a firmware, a software application, and a combination thereof. These various embodiments can include embodiment in one or more computer programs that are executable and/or interpretable on a programmable system including one programmable processor, which may be special or general purpose, coupled to receive data and instructions from, and to transmit data and instructions to, a storage system, one input device, and at least one output device.

These computer programs (also known as programs, software, software applications, and/or code) comprise machine-readable instructions for a programmable processor, and can be implemented in a high-level procedural and/or object-oriented programming language, and/or in assembly/machine language. As used herein, the terms "machine-readable medium" and/or "computer-readable medium" refers to any computer program product, apparatus and/or device (e.g., magnetic discs, optical disks, memory, and/or Programmable Logic Devices ("PLDs")) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here may be implemented on a computing device having a display device (e.g., a cathode ray tube ("CRT") and/or liquid crystal ("LCD") monitor) for displaying information to the user and a keyboard and a mouse by which the user can provide input to the computer. Other kinds of devices can be used to provide for interaction with a user as well; for example, feedback provided to the user can be any form of sensory feedback (e.g., visual feedback, auditory feedback, and/or tactile feedback) and input from the user can be received in any form, including acoustic, speech, and/or tactile input.

The systems and techniques described here may be implemented in a computing system that includes a back end component (e.g., as a data server), a middleware component (e.g., an application server), a front end component (e.g., a client computer having a graphical user interface, and/or a Web browser through which a user can interact with an embodiment of the systems and techniques described here), and a combination thereof. The components of the system may also be coupled through a communication network.

The communication network may include a local area network ("LAN") and a wide area network ("WAN") (e.g., the Internet). The computing system can include a client and a server. In one embodiment, the client and the server are remote from each other and interact through the communication network.

A number of embodiments have been described. Nevertheless, it will be understood that various modifications may be made without departing from the spirit and scope of the claimed invention. In addition, the logic flows depicted in the figures do not require the particular order shown, or sequential order, to achieve desirable results. In addition, other steps may be provided, or steps may be eliminated, from the described flows, and other components may be added to, or removed from, the described systems. Accordingly, other embodiments are within the scope of the following claims.

It may be appreciated that the various systems, methods, and apparatus disclosed herein may be embodied in a machine-readable medium and/or a machine accessible medium compatible with a data processing system (e.g., a computer system), and/or may be performed in any order.

The structures and modules in the figures may be shown as distinct and communicating with only a few specific structures and not others. The structures may be merged with each other, may perform overlapping functions, and may communicate with other structures not shown to be connected in the figures. Accordingly, the specification and/or drawings may be regarded in an illustrative rather than a restrictive sense.

Where the above examples, embodiments and implementations reference examples, it should be understood by those of ordinary skill in the art that other use case, execution environments, and data structures could be intermixed or substituted with those provided. In places where the description above refers to particular embodiments of a personalized therapy system or method, it should be readily apparent that a number of modifications may be made without departing from the spirit thereof and that these embodiments and implementations may be applied to other personalized therapy systems and methods as well. Accordingly, the disclosed subject matter is intended to embrace all such alterations, modifications and variations that fall within the spirit and scope of the disclosure and the knowledge of one of ordinary skill in the art.

The concepts disclosed herein are not limited to the specific examples shown herein. It should be readily apparent that a number of modifications may be made without departing from the spirit thereof and that these implementations may be applied to other implementations disclosed or undisclosed. The presently disclosed methods and systems are, therefore, to be considered in all respects as illustrative and not restrictive.

What is claimed is:

1. A system for creating a genetically personalized intravenous or intramuscular nutrition therapy treatment formula, the system comprising:
    a plurality of genetic testing kits, each testing kit configured to determine genetic information of one of a plurality of patients, the plurality of patients positioned geographically remotely from each other;

a plurality of electronic devices, each electronic device configured to receive the genetic information of one of the plurality of patients, medical information of the one of the plurality of patients, and therapeutic objectives of the one of the plurality of patients; and a server comprising a database storing a personalized nutrition therapy formula creation algorithm, wherein the server is configured to wirelessly receive the genetic information, the medical information, and the therapeutic objectives of each of the plurality of patients, wherein the server is configured to, for each of the plurality of patients:

output to the electronic device a custom intravenous or intramuscular nutrition therapy treatment formula for the patient from the personalized nutrition therapy formula creation algorithm based on the medical information, genetic information, and therapeutic objectives of the patient, wherein the ingredients of the custom intravenous or intramuscular nutrition therapy formula comprise one or more micronutrients identified by the personalized nutrition therapy formula creation algorithm as a match for the medical information, genetic information, and therapeutic objectives of the patient based on individual scores stored in the database of a plurality of existing individual scientific literature references relating to the one or more micronutrients and individual treatment scores stored in the database of previous intravenous or intramuscular nutrition therapy treatments comprising the one or more micronutrients, wherein the patient is treated with the custom intravenous or intramuscular nutrition therapy treatment formula;

receive feedback data about results of the custom intravenous or intramuscular nutrition therapy treatment formula after the patient has been treated based on the custom intravenous or intramuscular nutrition therapy treatment formula, wherein the feedback data comprises feedback about measured bloodwork, epigenetic changes, improvements or declines in symptoms, progress towards reaching therapeutic objectives, vital signs, overall health and fitness, or physical or mental energy;

create an individual treatment score based on the feedback data and store the individual treatment score in the database;

update the personalized nutrition therapy formula creation algorithm to incorporate the individual treatment score for subsequent patients; and create future custom intravenous or intramuscular nutrition therapy treatment formulas based on the updated personalized nutrition therapy formula creation algorithm, wherein the updated personalized nutrition therapy formula creation algorithm is configured to create custom intravenous or intramuscular nutrition therapy treatment formulas comprising micronutrients that most closely match patient needs based on all available patient medical information, genetic information, and therapeutic objectives, and most current aggregated feedback based on real patients with similar genes and symptoms.

2. The system of claim 1, wherein the therapeutic objectives comprise health goals, aesthetic goals, fitness goals, weight loss, increased energy, healthier skin, healthier hair, or improved mental acuity.

3. The system of claim 1, wherein the personalized nutrition therapy formula creation algorithm is configured to map the medical information and the genetic information to a code.

4. The system of claim 3, wherein the code comprises a selection from the International Classification of Diseases.

5. The system of claim 1, wherein the personalized nutrition therapy formula creation algorithm comprises multiple algorithms in sequence.

6. The system of claim 1, wherein the medical information comprises at least one current symptom and at least one condition.

7. The system of claim 1, wherein the medical information of a first patient of the plurality of patients comprises a first symptom and the genetic information of the first patient comprises a first gene, wherein the medical information of a second patient of the plurality of patients comprises the first symptom and the genetic information of the second patient comprises a second gene different than the first gene, and wherein the one or more micronutrients of the custom intravenous or intramuscular nutrition therapy treatment formula for the first patient comprises a first micronutrient and the one or more micronutrients of the custom intravenous or intramuscular nutrition therapy treatment formula for the second patient comprises a second micronutrient different than the first micronutrient.

8. A system for creating a genetically personalized intravenous or intramuscular nutrition therapy treatment formula, the system comprising:

a plurality of genetic testing kits, each testing kit configured to determine genetic information of one of a plurality of patients;

a plurality of electronic devices, each electronic device configured to receive the genetic information of one of the plurality of patients, medical information of the one of the plurality of patients, and therapeutic objectives of the one of the plurality of patients; and a server comprising a database storing a personalized nutrition therapy formula creation algorithm, wherein the server is configured to wirelessly receive the genetic information, the medical information, and the therapeutic objectives of each of the plurality of patients, wherein the server is configured to, for each of the plurality of patients:

output to the electronic device a custom intravenous or intramuscular nutrition therapy treatment formula for the patient from the personalized nutrition therapy formula creation algorithm based on the medical information, genetic information, and therapeutic objectives of the patient, wherein the ingredients of the custom intravenous or intramuscular nutrition therapy formula comprise one or more micronutrients identified by the personalized nutrition therapy formula creation algorithm as a match for the medical information, genetic information, and therapeutic objectives of the patient based on individual scores stored in the database of a plurality of existing individual scientific literature references relating to the one or more micronutrients and individual treatment scores stored in the database of previous intravenous or intramuscular nutrition therapy treatments comprising the one or more micronutrients, wherein the patient is treated with the custom intravenous or intramuscular nutrition therapy treatment formula;

receive feedback data about results of the custom intravenous or intramuscular nutrition therapy treatment formula after the patient has been treated based on the custom intravenous or intramuscular nutrition therapy treatment formula;

create an individual treatment score based on the feedback data and store the individual treatment score in the database;

update the personalized nutrition therapy formula creation algorithm to incorporate the individual treatment score for subsequent patients; and create future custom intravenous or intramuscular nutrition therapy treatment formulas based on the updated personalized nutrition therapy formula creation algorithm.

9. The system of claim 8, wherein the plurality of patients are positioned geographically remotely from each other.

10. The system of claim 8, wherein the feedback data comprises feedback about measured bloodwork, epigenetic changes, improvements or declines in symptoms, progress towards reaching therapeutic objectives, vital signs, overall health and fitness, or physical or mental energy.

11. The system of claim 8, wherein the updated personalized nutrition therapy formula creation algorithm is configured to create custom intravenous or intramuscular nutrition therapy treatment formulas comprising micronutrients that most closely match patient needs based on all available patient medical information, genetic information, and therapeutic objectives, and most current aggregated feedback based on real patients with similar genes and symptoms.

12. The system of claim 8, wherein the medical information comprises at least one current symptom and at least one condition.

13. The system of claim 8, wherein the personalized nutrition therapy formula creation algorithm comprises multiple algorithms in sequence.

14. A system for creating a genetically personalized intravenous or intramuscular nutrition therapy treatment formula, the system comprising:

a plurality of genetic testing kits, each testing kit configured to determine genetic information of one of a plurality of patients; and a server comprising:

a database comprising a personalized nutrition therapy formula creation algorithm; and a processor, the processor coupled to a network and configured to receive the genetic information of the plurality of patients, medical information of the plurality of patients, and therapeutic objectives of the plurality of patients;

wherein the server is configured to output to an electronic device a custom intravenous or intramuscular nutrition therapy treatment formula for a patient of the plurality of patients from the personalized nutrition therapy formula creation algorithm based on the medical information, genetic information, and therapeutic objectives of the patient, wherein the ingredients of the custom intravenous or intramuscular nutrition therapy formula comprise one or more micronutrients identified by the personalized nutrition therapy formula creation algorithm as a match for the medical information, genetic information, and therapeutic objectives of the patient based on individual scores stored in the database of a plurality of existing individual scientific literature references relating to the one or more micronutrients and individual treatment scores stored in the database of previous intravenous or intramuscular nutrition therapy treatments comprising the one or more micronutrients, wherein the patient is treated with the custom intravenous or intramuscular nutrition therapy treatment formula, wherein the processor is further configured to receive feedback data about results of the custom intravenous or intramuscular nutrition therapy treatment formula after the patient has been treated based on the custom intravenous or intramuscular nutrition therapy treatment formula, wherein the processor is further configured to create an individual treatment score based on the feedback data and store the individual treatment score in the database, and wherein the processor is configured to update the personalized nutrition therapy formula creation algorithm to incorporate the individual treatment score for subsequent patients.

15. The system of claim 14, wherein the feedback data comprises feedback about measured bloodwork, epigenetic changes, improvements or declines in symptoms, progress towards reaching therapeutic objectives, vital signs, overall health and fitness, or physical or mental energy.

16. The system of claim 14, wherein future custom intravenous or intramuscular nutrition therapy treatment formulas are created based on the updated personalized nutrition therapy formula creation algorithm.

17. The system of claim 14, wherein the updated personalized nutrition therapy formula creation algorithm is configured to create custom intravenous or intramuscular nutrition therapy treatment formulas comprising micronutrients that most closely match patient needs based on all available patient medical information, genetic information, and therapeutic objectives, and most current aggregated feedback based on real patients with similar genes and symptoms.

18. The system of claim 14, wherein the therapeutic objectives comprise health goals, aesthetic goals, fitness goals, weight loss, increased energy, healthier skin, healthier hair, or improved mental acuity.

19. The system of claim 14, wherein the personalized nutrition therapy formula creation algorithm is configured to map the medical information and the genetic information to a code.

20. The system of claim 19, wherein the code comprises a selection from the International Classification of Diseases.

* * * * *